United States Patent [19]
Fry et al.

[11] Patent Number: 5,792,663
[45] Date of Patent: Aug. 11, 1998

[54] HIGH EFFICIENCY CONTINUOUS FLOW THROUGH FRACTIONAL-VOLATILIZATION SEPARATOR SYSTEM, AND METHOD OF USE

[75] Inventors: Robert C. Fry; Michael R. Dyas; Jason A. Rivers; Robert M. Brown, Jr., all of Omaha, Nebr.

[73] Assignee: Transgenomic Incorporated, Omaha, Nebr.

[21] Appl. No.: 722,781

[22] Filed: Sep. 27, 1996

[51] Int. Cl.$^6$ .......................... G01N 33/20; G01N 21/00; G01N 1/10; B01D 1/22

[52] U.S. Cl. .................. 436/73; 436/79; 436/80; 436/81; 436/82; 436/171; 436/172; 436/173; 436/181; 422/99; 159/13.1; 159/13.2; 159/49

[58] Field of Search ............... 159/13.1, 13.2, 159/27.3, 43.1, 49; 422/99; 436/73, 79, 80, 81, 82, 171, 172, 173, 181

[56] References Cited

U.S. PATENT DOCUMENTS

| | | |
|---|---|---|
| 539,549 | 5/1895 | Schuman . |
| 1,784,169 | 4/1930 | Jahannsen . |
| 2,129,596 | 9/1938 | Waterman et al. ............. 159/49 X |
| 2,186,876 | 1/1940 | Menardi . |
| 2,336,430 | 12/1943 | Wery . |
| 2,483,623 | 10/1949 | Clayton ..................... 159/13.1 X |
| 3,175,962 | 3/1965 | Hotslag . |
| 3,530,923 | 9/1970 | Mattern ....................... 159/13.1 |
| 3,857,704 | 12/1974 | Coulter ............................. 75/121 |
| 4,002,432 | 1/1977 | Brice ................................ 23/284 |
| 4,281,246 | 7/1981 | White, V et al. ........... 159/13.1 X |
| 4,452,068 | 6/1984 | Loo .................................. 73/28 |
| 4,559,808 | 12/1985 | Sturman ............................ 73/23 |
| 4,962,276 | 10/1990 | Yan ................................ 585/867 |
| 5,112,442 | 5/1992 | Goodson ................... 159/27.4 X |
| 5,298,227 | 3/1994 | Hirth et al. ....................... 423/1 |
| 5,454,860 | 10/1995 | Zhu ............................... 96/202 |

OTHER PUBLICATIONS

C. E. Oda et al. *Anal. Chem.* 1981, 53, 2030–2033.
H. Morita et al. *Anal. Lett.* 1983, 16, 1187–1195.
N.E. Fagerholm et al. *Sci. Tech. Froid* 1985, 273–279.
I.D. Brindle et al. *Analyst* 1992, 117, 407–411.
C.P. Hanna et al. *J. Anal. At. Spectrom.* 1993, 8, 585–590.
S.T.G. Anderson et al. *J. Anal. At. Spectrom.* 1994, 9, 1107–1110.
A. Skoczylas et al. *Chem. Eng. J.* 1995, 56, 51–58.
K. Tuzla et al. *Exp. Heat Transfer* 1995, 8, 177–184.
Leeman Labs Inc. APIP5200 Automated Mercury System Marketing Flyer.
Scientific Measurements Systems Inc. Mercury Analyzer QS–1 Marketing Flyer.
Spectro Analytical Instruments—Mercury Analyzer Marketing Flyer.
Perkin Elmer Flow Injection Mercury System (FMS) Marketing Flyer.

*Primary Examiner*—Arlen Soderquist
*Attorney, Agent, or Firm*—James D. Welch

[57] ABSTRACT

Fractional-volatilization separation systems and methods are disclosed which enable a stable, continuous, non-bubbling liquid flow, essentially constant surface area/volume ratio, temperature controlled, fractional volatilization of volatile/semi-volatile components in a liquid analyte or component containing sample. The fractional volatilization separator system can be utilized in small scale analytical and large scale chemical purification, concentration and desalinization applications. Continuous rapid removal of residual liquid sample can provide concentrated non-volatile component/analyte solution, and allows quick and easy washout between sequential use with different liquid samples. Examples of relevant analytical chemistry applications of the present invention system are found in conjunction with long-path absorbance-cell "cold-vapor" mercury analyzers, cold vapor mercury fluorescense photometers, infrared spectrophotometers, organic mass spectrometers, plasma emission spectrometers, and plasma mass spectrometers.

30 Claims, 14 Drawing Sheets

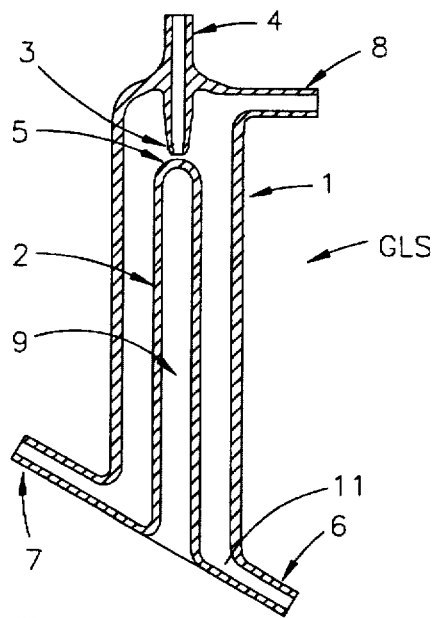
FIG. 5a₁
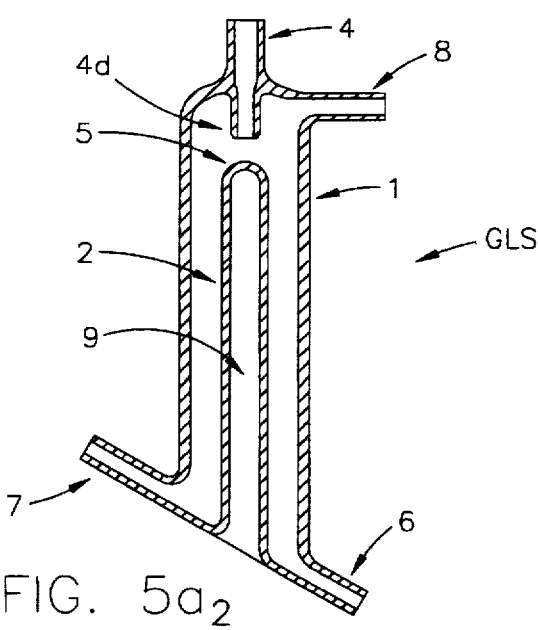
FIG. 5a₂
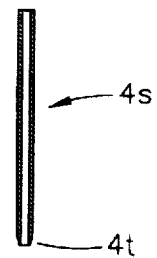
FIG. 5b₁
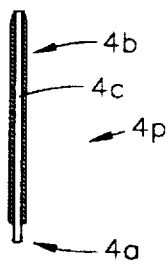
FIG. 5b₂
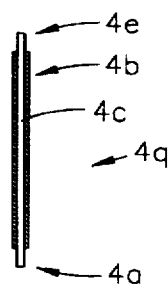
FIG. 5b₃

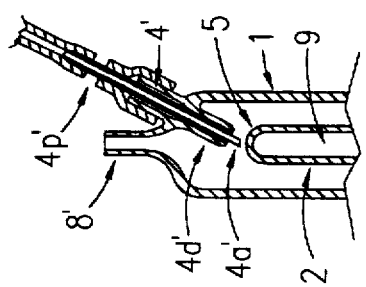
Fig. 5a6
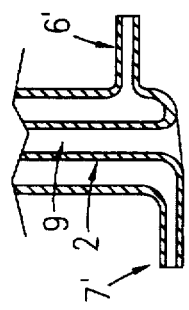
Fig. 5a10
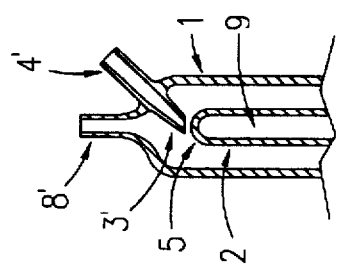
Fig. 5a5
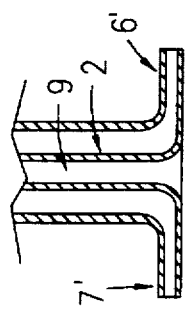
Fig. 5a9
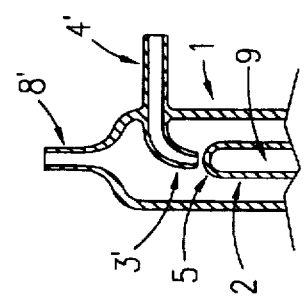
Fig. 5a4
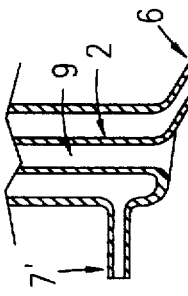
Fig. 5a8
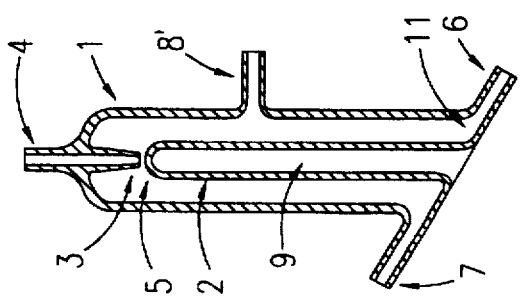
Fig. 5a3
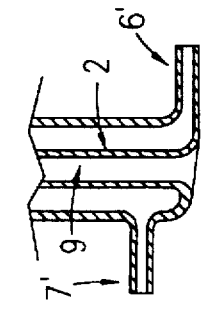
Fig. 5a7

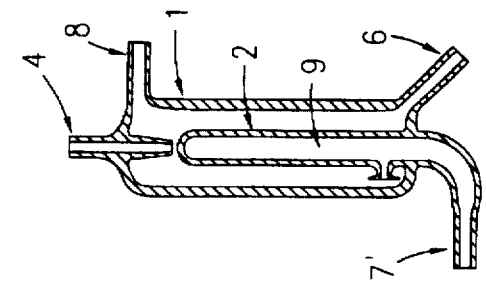
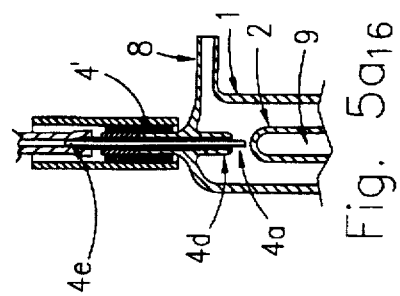
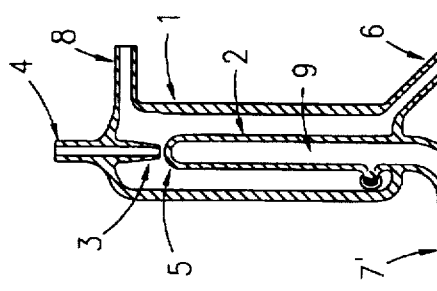
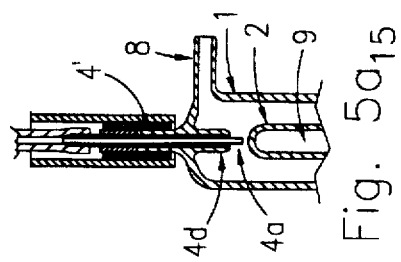
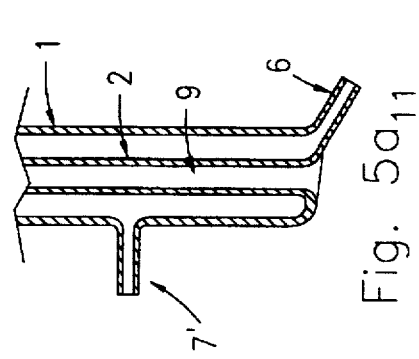
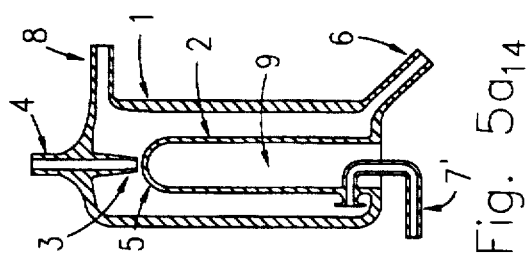

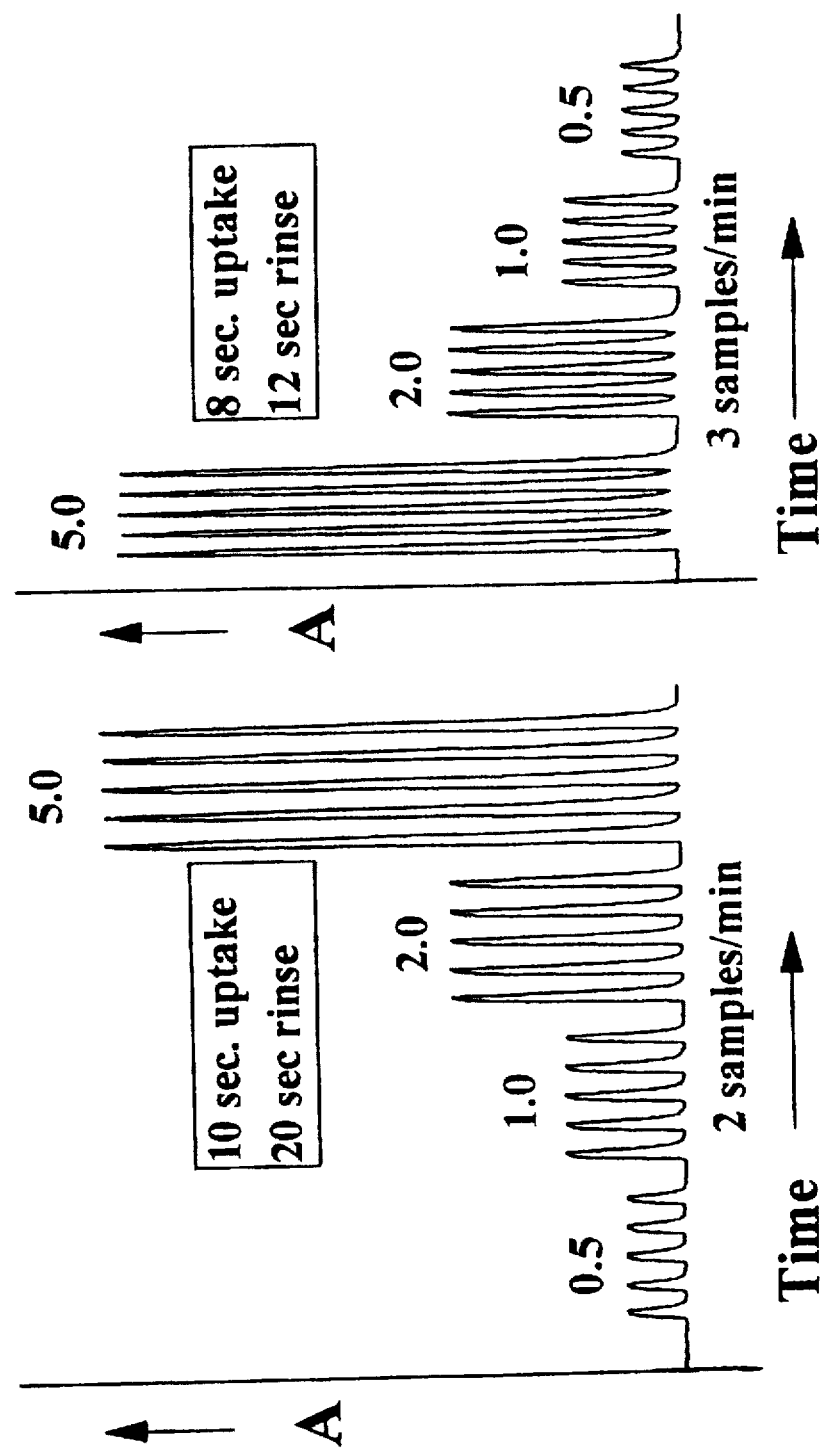

HIGH EFFICIENCY CONTINUOUS FLOW THROUGH FRACTIONAL-VOLATILIZATION SEPARATOR SYSTEM, AND METHOD OF USE

TECHNICAL FIELD

The present invention relates to small and large scale gas-liquid separator and fractional-volatilization separator systems, and methods of use. More particularly, the present invention is primarily a fractional-volatilization separator system which enables a stable continuous flow, essentially constant surface area/volume ratio, optionally temperature controlled, fractional-volatilization of volatile or semivolatile component(s)/analyte(s) in a liquid sample solution and/or emulsion and/or mixture and the like. The present invention fractional-volatilization separator system can be equally well utilized in analytical chemistry, chemical purification, preparation of liquid concentrate, in industrial procedures and where present component(s)/analyte(s) of interest are either more less volatile than the containing liquid, and are present in majority, minority or trace amounts.

BACKGROUND

One of the first system embodiments for use in phase separation, was a simple fractional distillation system comprised of a boiling-pot and a condenser. By use of said simple system a volatile component, (or alternatively "analyte"), or solvent contained in a liquid sample solution or mixture can be removed therefrom by simply adjusting the temperature of the boiling pot to the point where said component/analyte is selectively vaporized, followed by directing said vapor to said condenser, wherein said component/analyte or solvent can be collected in a concentrated form. Alternatively viewed, it can be stated that "less-volatile" component/analyte or solvent remaining in said boiling pot becomes "purified" of an evaporating "more-volatile" component/analyte or solvent by said procedure. Such boiling-pot and condenser systems, however, are difficult to apply in continuous flow-through applications, and changing liquid component/analyte containing sample solutions therein presents cross-contamination problems and logistical inconvenience, in the context of analytical chemistry. As well, boiling-pot and condenser systems are not conducive to sub-boiling point, differential vapor pressure based separations, which, it is noted, often provide the highest purity results. As well, the end result, being in a condensed liquid, rather than in a gaseous phase, is often not optimum for use in spectrometric identification and analysis, which approach frequently works best with gaseous phase samples.

Another approach to fractional-volatilization involves use of a bubbler-style, sub-boiling point distillation system. Such bubbler-style systems cause a gas to bubble through a liquid mixture or component or analyte-containing liquid sample solution. Said bubbling gas flow causes components or analytes to evaporate from, (and leave), said liquid sample solution and enter analytical instruments, or to enter a head space in the bubbler-style system. Bubbling action, however, can lead to hydraulic transient-caused instabilities in associated analytical instruments, and can cause foaming and frothing of certain liquid sample solutions. Another problem is that wash-out time, (which is required when liquid samples solutions are changed, to avoid cross-contamination), in bubbler-style systems, can be excessively long. As well, it can be difficult to accurately control temperature in sub-boiling point distillation procedures. This can make precise production process control, medium scale separation and chemical analysis procedures difficult.

Yet another approach to sub-boiling distillation involves rotary evaporators in which centripetal force is utilized to force a liquid to spread up onto the interior side walls of a round bottomed flask. This serves to increase evaporation by increasing the surface area of a liquid component or analyte containing sample solution by forcing it to spread into a film geometry which may be accompanied by directing a flow of carrier gas against or along said liquid film to accelerate removal of evaporated vapors. Systems utilizing this approach, however, require prohibitively long wash-out times when liquid component or analyte containing sample solutions are changed. As well, it is difficult to precisely control the temperature of a liquid component or analyte containing sample solution to which is being imparted rotary motion. Further, it is noted that a rotary evaporator is a "batch", rather than a continuous flow-through processor. This means that as a rotary evaporation proceeds, a vapor provided thereby continuously provides lower and lower concentrations of sample components or analytes. The volatile component or analyte output concentration therefore changes over time. Finally, the batch nature of the process makes sample changing tedious and awkward.

Still another approach to separation of components or analytes from a liquid sample solution is that of gas-liquid chromatography (GLC), or frequently identified as simply (GC). This approach, however, is capable of handling only relatively small amounts of liquid sample solution, (eg. typically a few nanoliters or microliters), and as such has been limited in application to the area of analytical chemistry. This technique provides that a small amount of liquid sample solution be entered to a heated injection port where all analytes are simultaneously "flash-evaporated" into a stream of carrier gas, (eg. nitrogen, argon, helium, hydrogen etc.) Said carrier gas then propels said "plug" of vapors into a relatively long, narrow-bore column containing a nonvolatile wax, oil etc. coating on a wall thereof. Alternatively a column can be packed with a porous or granular solid substrate, which may be coated with a nonvolatile wax or oil et.c. The carrier-gas is referred to as a "mobile-phase" and the coating oil nonvolatile wax, oil or other material, or the coated column packing, is referred to as the "stationary" phase. In use, the temperature of the column can be user-set to optimize volatile component separation. As the mobile phase causes the analyte containing vapors to proceed through the column, volatile components therein typically interact "reversibly" with said stationary phase. Separation of migrating analytes occurs because varied interaction strength or volatility causes each analyte to migrate at a different rate. Gas-liquid chromatography separation thus occurs over time. Although such gas-liquid separations can be among the best possible under favorable conditions, and even though only small quantities of liquid sample solution are necessary, there remain problems involved in practice of the technique. One such problem is that large samples, (larger than a few microliters), can not be readily processed. As well, at times small amounts of liquid sample solution, (eg. a few microliters), are insufficient to allow reasonable detection, identification and quantitative determination of certain analytes contained therein by, for instance, infrared spectrometer detection of organic substances. In addition, as gas chromatography systems deliver analyte vapors at the end of a narrow-bore column in batches, often the "batch-time", (over which an analyte vapor is available), is too short to allow accurate infrared scans, with high signal to noise ratio and high spectral resolution. To utilize such "batch" available analyte vapors, infrared scans must be very fast, and this often prohibits the obtaining of high resolution and Fourier Transform Infra-Fed (FTIR) scans which can significantly enhance analytical detection limits of organic components by signal averaging over extended times.

Continuing, another very relevant application of gas-liquid separator systems is in the analysis of liquid sample solutions which contain mercury, such as by long-path absorbance-cell systems. When a gas-liquid separator is so applied, a mercury containing liquid sample solution is typically treated with a chemical, such as, but not limited to, stannous chloride. This serves to convert ionic mercury to a "cold vapor" volatile $Hg^0$ form, (rather than its original $Hg^{2+}$, form). After such treatment, traces of mercury are presumed to be present as a finely-dispersed emulsion of tiny liquid micro-droplets of $Hg^0$ suspended in an aqueous sample solution. Much of the known art involving gas-liquid separators for use in "cold vapor" mercury analyzers is summarized in the United States Environmental Protection Agency (EPA) Analytical Method No. 245.1. Said report shows that original "cold vapor" mercury analyzers employed a glass-frit gas bubbler to sparge, (ie. degass), mercury vapor traces from a pretreated mercury-containing liquid sample solution. Said EPA report states that liquid mercury containing sample solutions are typically contained in a Biological Oxygen Demand (BOD), or other flask, container with a volume on the order of sixty (60) to three-hundred (300) milliliters, when subjected to chemical reduction with stannous chloride and said gas "sparging". In reported systems, immediately after treatment with stannous chloride, (or other reductant), a gas bubbler is plunged below the liquid sample solution surface, and the container stoppered; a remaining gas escape route being through a gas transfer tube. Air or nitrogen is bubbled through the liquid sample solution and $Hg^0$ (liquid) is caused, by evaporation, to become $Hg^0$ (vapor). Once $Hg^0$ (vapor) is available it is swept into an optical gas cell, where analysis via atomic absorption, emission or fluorescence procedures, and/or by ultraviolet spectrum analysis is conducted. Typically, excitation of said $Hg^0$ (vapor) is by exposure to two-hundred-fifty-four (254 ) nanometer wavelength radiation from a mercury "lamp", or by exposure to "collisional excitation" in a radio frequency powered, hot (excited), argon plasma, (eg. an inductively coupled plasma-(ICP). Spectral isolation can be via UV filter, prism, or diffraction grating, and detection is typically by silicon photo-detectors, high voltage photo-tubes, or photomultiplier tube detectors. To accurately measure mercury levels, a system is calibrated with known precalibrated reference samples. Unknown samples are then investigated by reference of their detector response to that of said precalibrated reference sample results. The cited EPA method is based in the fact that said "cold vapor" analytical method achieves substantial gas-phase mercury enrichment factors which enhance the measuring analytical sensitivity considerably. Said "cold vapor" EPA method is capable of detecting about 0.2 parts-per-billion of $Hg^{2+}$in drinking water. Urine, blood, soil and a variety if other liquid and solid samples can also be analyzed if they are subjected to prior treatment with oxidizing agents such as potassium permaganate and/or hot mineral acid to liberate $Hg^{2+}$ions from organic binding agents into solution prior to, stannous chloride, (or other reductant), treatment for conversion to $Hg^0$.

As described infra, certain problems exist where a "bubbler" system is employed. In the presently discussed context, such problems are based in the presence of hydraulic noise transients, instability, unpredictability of the liquid analyte containing sample solution surface-area-to-volume ratio, and short term degassing rate changes which induce variations in photo-detector response. Bubbler action can also cause foaming or frothing in certain prepared samples, such as urine, blood and fish tissue digests. In addition, readings obtained using a BOD, or equivalent flask, container are inherently less than reproducible, as human action is involved in placing a bubbler thereinto, and plugging said BOD, or equivalent flasks, container. One user might act with faster response time than another, for instance. A variable amount of present mercury can be lost to the atmosphere as a result. In addition, certain ratios, such as the surface area/volume ratio for a liquid analyte containing sample solution can vary where a BOD, or equivalent flask, container is utilized. Vigorous bubbling can serve to improve said ratio, but that can lead to destabilized detector readings, due to signal transients introduced by the bubbling action.

More recent systems for analyzing sample solution mercury content provide that stannous chloride solution be continuously mixed with liquid mercury containing sample solution via a mixing "Tee", located prior to the gas-liquid separator. Such can involve sample segmentation by intervening air spaces. Other systems, such as a system marketed by Perkin-Elmer Corp. provide that a sample "bolus" be pre-loaded into a loop of tubing, then, via a multi-port valving system, switched into a continuously flowing stream of rinsing fluid. The resulting bolus is then caused to progress toward a mixing, "Tee" without the requirement that air spaces be present for segmentation. Whichever approach is utilized to this point, liquid mercury containing sample solution is typically pumped to a small plumbing "Tee" whereat stannolus chloride, (or other reductant), is mixed therewith. Following this, said mixture is pumped to a second "Tee" whereat a gas is caused to mix therewith, by being bubbling therethrough, just prior to being injected into a gas-liquid separator system. Leeman Labs Inc. provides a gas-liquid separator in which a liquid reservoir is present. A Liquid mixture entered thereto fills said reservoir from the bottom upward, and in use gas is bubbled upward through said liquid mixture which accumulates therein. Spent (reacted) liquid sample solution exits via a spill-over port located at a top of said reservoir system. Evaporated mercury vapor also exits with the carrier gas via another "Topside" port located near thereto. Problems in use of said Leeman Labs Inc. system develop because a substantial volume of the spent reacted liquid sample solution accumulates in the reservoir prior to spill-over removal, and both mercury vapor and transporting carrying gas flow must bubble therethrough. Bubbling is an erratic process which causes system "noise" and instability, as well as undesirable foaming side effects with certain sample types. Other gas-liquid separator systems fail to provide a stable predictable surface area over which a liquid analyte containing sample solution will flow in use. Such systems provide a surface area, but do not provide means to assure all provided surface area will be wetted and support a continuous smooth flow thereover of constant average surface area in use. With incomplete surface area coverage, a liquid analyte containing sample solution tends to variously wander, unpredictably, over portions or fractions of the available surface area in such systems. This gives rise to system instability and non-reproduciblity of results, as well causing the necessity for extended washout time between samples.

A primary disadvantage of all known prior gas-liquid separators, however, is that they are generally not thermally stabilized. This is of particular importance in analytical chemistry because variations in temperature can alter vapor pressures cover the course of an hour or so. This leads to uncompensated variations in calibration, and leads to errors in results of tests conducted on unknown samples. In known gas-liquid separator systems the surface area over which a stannous-chloride-treated, liquid-mercury-containing sample system, for instance, flows, is but a gas-liquid separator system "wall thickness away" from a room or instrument cabinet ambient, and thus susceptible to influence by temperature changes which occur in said room or instrument cabinet ambient.

With the present invention in mind, a Search of Patents for systems utilized in gas-liquid separation was conducted and has provided the following results:

A U.S. Pat. No. 5,298,227 to Hirth et al. is identified because it describes a carrier gas passed over a melt. The Patent mentions industrial scale usage. Mercury is mentioned as a separable component. However, the system is not structurally particularly relevant.

Next, U.S. Pat. No. 4,962,276 to Yan was discovered and is disclosed because it describes a process for removing mercury from water or hydrocarbon, in which a condensate is sprayed into a stripper system. The structure of the system is not particularly relevant, and operation is via the spraying or misting, rather than by formation of a liquid film.

A U.S. Pat. No. 4,452,068 to, Loo was identified and is disclosed as FIG. 2 thereof shows an air sample inlet arrangement, and an upward facing impactor for removing solid particles, and water drops downward therefrom in streams. The structure of the Loo system is minimally relevant, and there is no mention of application in a fractional-volatilization setting in which analytes or components are exited into a carrier gas stream.

A Coulter U.S. Pat. No. 3,875,704 is disclosed as it shows a downward sloping system for effecting a film of liquid in use in FIG. 2 thereof. However, structural relevance is minimal as there is neither a convex surface, nor an apex present. Separation is achieved by bubbling inert gas or injecting live steam through a liquid present in a reservoir. It is noted that liquid film present on sloping sections is utilized only for transfer means between reservoirs wherein evaporation occurs.

Next, a Hotslag U.S. Pat. No. 3,175,962 is disclosed as it shows a means over which a liquid film, (distalland), flows in a downward manner in use. Heat is applied thereto, and a portion thereof vaporizes and it is carried along in a stream. A liquid film, however, forms on a concave side of a protrusion and there is no identifiable apex present.

A Menardi U.S. Pat. No. 2,186,876 shows a system for removing mercury from ores. A heated gas is caused to flow over heated solid ore in a rotating kiln and carries off mercury vapor which is formed. Liquid is not involved in the evaporation, and the evaporating surface is concave, with no apex.

U.S. Pat. No. 1,754,169 to Jahannsen is another ore handling system in which a gas flow carries away gassifiable vapors. Liquid is not involved and the evaporation surface is concave with no apex present.

U.S. Pat. No. 539,549 to Schuman is disclosed because it shows a conical spreading cone a bit like a convex protrusion. See FIG. 2 therein. However, neither liquid, nor evaporation, nor carrier gas is involved.

A Wery U.S. Pat. No. 2,336,430 is included because it shows a Cone a bit like a convex protrusion. The purpose thereof is to deflect liquid flowing thereover to redirect said liquid to contact and flow over the concave inner wall of a cylindrical element in which the cone is present, and by which it is surrounded. While there is present a cone with an apex, said cone is utilized only as a high-speed deflector to redirect sample against a second surface, which is an inner chamber wall and which is concave with no apex. There is no mention of a use of a tangentially flowing carrier gas, and gasses simply diffuse out of said liquid which drains down said inner concave wall of a cylindrical element surrounding said deflector cone.

A Brice U.S. Pat. No. 4,002,432 describes a system which is similar in important respects to the Wery Patent system. However, the system structure is relatively complex and there is no auxiliary counterflow of carrier gas described.

A Sturman U.S. Pat. No. 4,559,808 shows a gas/liquid Separator. A liquid/gas stream is caused to impact the side of an upstanding tube in the center of a chamber, which tube has a surface which has been treated to encourage adhesion of the liquid component. The system requires that, in use, liquid be entered through a side of a chamber thereof and that a carrier gas be entered into, an upper region of said chamber, above present liquid which collects in the bottom of said chamber, resulting in a liquid level and spill-out into a second chamber, which is utilized in drainage. While an apex structure is present, it is not closed, (gas enters through it in use), it does not serve to spread a liquid, and liquid is not applied directly to said apex in use.

Finally a Zhu U.S. Pat. No. 5,454,860, describes the flow of a liquid in a sheet over a surface area providing means, and describes quick and immediate removal of liquid. However, the Zhu system does not employ a convex protrusion or an apex and it does not employ complete surface area coverage of an evaporation surface by a liquid. The Zhu system employs a gas-liquid mixture with quantized bubbling, and operates at an elevated internal pressure which serves to average out fluctuations effected by quantized bubble formation of gaseous analyte.

There remains need for a fractional-volatilization separator system which serves to overcome problems identified in the foregoing, particularly as regards the providing of a stable predictable surface area/volume ratio for a liquid analyte containing sample solution formed film, and as regards enabling rapid washout time where sample change is effected, and as regards elimination of the need for bubbling action, and as regards stabilization of the temperature of the surface area in said fractional-volatilization separator system over which said liquid component/analyte containing sample solution formed film flows in use, while component/ analyte vapors are evaporated therefrom. Such a fractional-volatilization separator system should be equally applicable in methods of practicing analytical chemistry and in practicing methods applicable in industrial settings including desalination, mixture separation, component isolation, purification, and the preparation of liquid concentrates.

DISCLOSURE OF THE INVENTION

The present invention system is a fractional-volatilization separator system, (said terminology to be broadly interpreted herein to encompass gas-liquid separators, fractional-volatilization separators, liquid purifiers, liquid concentrators, desalination systems etc., including various combinations thereof, for use in analytical chemistry and industrial settings), comprising an outer envelope, which in the preferred embodiment is elongated, the elongated dimension of which is, in use, oriented essentially vertically.

Said preferred embodiment of said fractional-volatilization separator system further comprises a surface area providing upward protruding essentially convex protrusion essentially centrally positioned within a thermally insulating space concentrically defined by said outer envelope. Said surface area providing essentially convex protrusion, in the preferred embodiment is also elongated, upward protruding and in comprises a closed upper apex. (It is noted that each of said outer envelope and surface area providing essentially convex protrusion can each be independently selected to be essentially rod, essentially sharp pencil, essentially blunt pencil, essentially pyramidal, essentially closed-top cylindrical, essentially conical, essentially spherical, essentially hemispherical, essentially "Washington Monument", essentially closed top hour-glass, essentially closed top multiple repeating hour glass, essentially bullet, essentially helical screw-thread shaped or of any functional shape, including non-elongated shapes and shapes including small flat portions at the upper aspect thereof. It is noted that functional shapes can include various combinations of said shapes as well as long as the end result is an essentially convex protrusion). Focusing upon the preferred embodiment, it is to be understood that the elongated surface area providing essentially convex protrusion and said elongated dimension outer envelope are essentially continuous at the lower extents thereof. Said fractional-volatilization separator system further comprises, at an "essentially closed" upper extent of said elongated dimension outer envelope, a liquid sample inlet means for introducing liquid component/analyte containing sample solution thereto such that in use, introduced liquid component/analyte containing sample solution is caused to be continuously, (during an analysis procedure measurement period); applied to an apex of said elongated surface area providing essentially convex protrusion and essentially uniformly spread and flow downward over the surface area provided by said elongated surface area providing essentially convex protrusion to the lower extent of said fractional-volatilization separator system, whereat said elongated dimension outer envelope and said elongated surface area providing essentially convex protrusion are essentially continuous. (It is noted that said elongated surface area providing essentially convex protrusion is closed, providing an apex surface at the upper aspect thereof). While said liquid component/analyte containing sample solution flows downward over said surface area provided by said elongated surface area providing essentially convex protrusion said liquid component/analyte containing sample solution is caused to form a continuous film of liquid component/analyte containing sample solution. It is noted that in the preferred embodiment, said continuous liquid film is typically found to be relatively thin, but it essentially completely covers the surface area provided by said surface area providing essentially convex protrusion, and it is further noted that said surface area providing essentially convex protrusion is preferably of a size so, as to occupy a substantial portion of the space confined by said outer envelope. It is to be understood that such film geometry encourages volatile component/analyte(s) present therein to evaporate efficiently therefrom. The fractional-volatilization separator system further comprises a means for quickly removing "residual" liquid sample from which has been evaporated volatile component/analyte, (and which can be described as "spent", "concentrated", "enriched" or "purified"), said means for quickly, and continuously, removing liquid sample being present, (while still in an essentially film geometry), at a lower extent collection site of said fractional-volatilization separator system where said elongated dimension counter envelope and said elongated surface area providing essentially convex protrusion are essentially continuous. In the preferred embodiment, at said lower extent where said elongated outer envelope and said elongated surface area providing essentially convex protrusion are essentially continuous, the lower perimeter of said surface area providing essentially convex protrusion is preferably relatively small, providing for relatively small liquid film boundary perimeter, although the surface area of the elongated surface area providing essentially convex protrusion is relatively large. There is also, preferably, present a sloping and/or channeling means for guiding "residual", "spent", "concentrated" or "enriched" liquid sample solution from which has been evaporated volatile component/analyte, to a single focused collection site for removal thereof via a means for quickly removing liquid sample, said removable means being of geometry to, abruptly focus, or transfer liquid film geometry into bulk tubular flow geometry immediately following removal through said fractional-volatilization separator system outer envelope geometry. Said fractional-volatilization separator system further provides means for entering a flow, (to be interpreted to include counter-flow), of carrier gas located near the lower extent of said fractional-volatilization separator system where said elongated dimension cuter envelope and said elongated surface area providing essentially convex protrusion are essentially continuous, as well as upper extent means for allowing said entered carrier gas to exit said fractional-volatilization separator system near said liquid sample inlet means for introducing liquid component/analyte containing sample solution. In use, evaporated volatile component(s)/analyte(s) which evaporate(s) from said liquid component(s)/analyte(s) containing sample solution is/are caused to accompany said carrier gas out of said means for allowing said entered carrier gas to exit said fractional-volatilization separator system.

It is to be noted that, in a preferred embodiment, the surface area of said elongated surface area providing essentially convex protrusion can be of a phillic nature with respect to said liquid component/analyte containing sample solution so as to encourage wetting thereof, film formation thereon, and the uniform sheeting and flow of said liquid component/analyte containing sample solution downward thereover in use. The preferred phillic nature can be effected or enhanced by control of the surface composition and/or surface texture of the surface area provided by said elongated surface area providing essentially convex protrusion. For instance, a glass surface area providing essentially convex protrusion can be phillic to water based liquids, and said phillic nature can be enhanced if said glass surface is roughened by sand blasting or "frosted" by hydrofluoric acid etching, or subjected to silanization or other chemical treatment.

It is to be understood that, in use, under the influence of gravity, a liquid component/analyte containing sample solution entered via said liquid sample inlet means for introducing liquid component/analyte containing sample solution, is caused to be continuously dispensed downward into the apex of said elongated surface area providing essentially convex protrusion in a manner which promotes uniform spreading and smooth, continuous, unbroken downward sheeting action over the surface area of said elongated upward protruding surface area providing essentially convex protrusion. That is, the apex of said elongated surface area providing essentially convex protrusion and a vertically superior dispensing tip of said liquid sample inlet means for introducing liquid component/analyte containing sample solution, are appropriately oriented with respect to one another so as to enable provision, by means of proximity appropriate to the surface tension and dispensing rate of the liquid present, of a continuous downward unbroken stream of liquid component/analyte containing sample solution between said vertically superior dispensing tip of said liquid sample inlet means and said vertically subordinate apex of said elongated surface area providing essentially convex protrusion.

The preferred outer dimensions of a present invention system for use in analytical chemistry procedures typically measure approximately sixty (60) millimeters long by fourteen (14) millimeters in diameter, with the elongated surface area providing essentially convex protrusion measuring approximately forty-four (44) millimeters long by five (5) millimeters in diameters (It is mentioned that a present invention system for use in commercial settings will typically be of larger dimensions). As well, the gap between the dispensing tip of the liquid sample inlet means for introducing liquid component/analyte containing sample solution, and the apex of said elongated surface area providing essentially convex protrusion, is typically approximately one-half (0.5) millimeter long, (ie. in the range of 0.2 to 0.8 millimeters when a water based sample solution flow rate on the order of four (4) milliliters/minute is used). However, it is noted that in some embodiments the gap is user adjustable, to accommodate a variety of sample liquids, surface tensions, and flow rates. That is, in various invention embodiments the liquid sample delivery means for introducing liquid component/analyte containing sample solution thereto can be fixed, or vertically movable upward and downward, through a sliding seal hole guide means present at and through the liquid sample introduction means, typically present at the location of the essentially closed upper extent of said elongated dimension outer envelope, at any location vertically superior to the apex if said surface area convex protrusion. However, a more common approach to effecting continuous flow of liquid component/analyte containing sample solution from said liquid sample inlet means for introducing liquid component/analyte containing sample solution, to the apex of said elongated surface area providing essentially convex protrusion, is to vary the flow rate of liquid component/analyte containing sample solution in a fixed gap system, said flow rate being selected according to the liquid sample solution surface tension and the surface area provided by the surface area providing essentially convex protrusion. An appropriate flow rate for optimum operation depends upon such factors as gap width, surface composition, and texture of the elongated surface area providing essentially convex protrusion, as well as surface tension of composite liquid component/analyte containing sample solution.

When the "residual", "spent", "concentrated", "enriched" or "purified" liquid sample solution from which component (s)/analyte(s) have been evaporated reaches the collection site, located in said fractional-volatilization separator system where said elongated dimension outer envelope and said elongated surface area providing essentially convex protrusion are essentially continuous), said liquid sample solution is caused to be quickly and continuously removed via a typically vertically lower-most positioned means for quickly removing liquid sample present at said collection site. This action prevents the accumulation of liquid sample solution, and what would otherwise, constitute a surface area providing essentially convex protrusion surface area reducing "flooding" effect at and above the collection sites. Said configuration also allows exceptionally fast washout and easy component/analyte sample change without residual sample carry-over problems, because said liquid sample solution can not accumulate. As well, said quick removal of liquid sample prevents blockage of the means for entering a flow of carrier gas located near the lower extent of, (but typically located in a vertically superior position with respect to the means for quickly removing liquid sample), said fractional-volatilization separator system where said elongated dimension outer envelope and said elongated surface area providing essentially convex protrusion are essentially continuous. Such also prevents carrier gas being forced to be entered through accumulated liquid sample solution, which if not prevented, can lead to undesirable "bubbling" and "foaming" as described in the Background Section of this Disclosure.

As well, the fractional-volatilization separator system elongated surface area providing essentially convex protrusion is preferably hollow, and optionally included therewithin is a temperature control means which optionally comprises a thermoelectric heating or cooling temperature controlling device. A hollow elongated surface area providing essentially convex protrusion can also be filled with insulating material, or with a material selected from the group consisting of a gas, a fluid, a paste, a gel or the like, which material can be subjected to temperature control during use.

It is to be appreciated that the elongated surface area providing essentially convex protrusion is shielded from the environment on its outer, wetted essentially convex, surface, by the space contained within said elongated dimension outer envelope, and optionally by said temperature control means and/or recited materials within its hollow space inner surface. This thermally enhanceea and optionally enhances a user's ability to control and stabilize the temperature of said wetted surface area of said surface area providing essentially convex protrusion in use. This, it must be understood allows a user very precise control cover evaporation rate and over what component and/or analyte in a liquid sample solution is, in fact, vaporized at a certain time. It is re-emphasized that the described geometrical arrangement of a surface area providing essentially convex protrusion, shielded from the outer environment on its wetted essentially convex outer surface area by the space contained within an outer envelope, and optionally shielded on its hollow space inner surface by, for instance, temperature control means, is an important attribute of the present invention fractional-volatilization system.

It is also noted that in the preferred embodiment, the means for entering a flow of carrier gas, (typically termed a "counter-flow" as it flows in a direction opposite to entered liquid analyte/-component containing sample solution), as well as said means for allowing said entered carrier gas to exit said fractional-volatilization separator system are typically oriented so as to cause carrier gas entered and exited thereby respectively, to follow a tangentially oriented spiral path, in close proximity to, and around, said surface area of said elongated surface area providing essentially convex protrusion. Such a tangential counter-flow locus of carrier gas further encourages efficient evaporation of component/analyte dissolved or emulsified etc. in said liquid sample solution film. Combined with precise temperature control of said surface area of said elongated surface area providing essentially convex protrusion, and the formation of a film of component/analyte containing sample solution, it is again noted that it becomes possible to selectively, and efficiently, volatilize and remove specific component/analytes or mixture components.

Prior to outlining a method of operation of said present invention it is to be understood that the foregoing has disclosed preferred embodiments of the present invention fractional-volatilization separator system. The present invention can be described in more general terms, as comprising an outer envelope and an upward protruding surface area providing essentially convex protrusion essentially centrally positioned within a space concentrically defined by said outer envelope. The surface area providing essentially convex protrusion and said outer envelope being essentially continuous at vertically lower extents thereof. The present invention fractional-volatilization separator system further comprises a liquid sample inlet means for use in introducing liquid component/analyte containing sample, such that in use, liquid component/analyte containing sample introduced therethrough is caused to be applied to an apex of said surface area providing essentially convex protrusion, and essentially uniformly spread and flow downward over the surface area provided by said surface area providing essentially convex protrusion as a film. This encourages volatile/semi-volatile component/analyte present therein to evaporate therefrom. The liquid component/analyte containing sample flow as a film downward ends, however, at a lower extent collection site of said fractional-volatilization separator system located essentially where said vertically lower extents of said outer envelope and said surface area providing essentially convex protrusion are essentially continuous. The fractional-volatilization separator system further comprises a means for quickly removing liquid sample, from which liquid sample has been evaporated volatile/semi-volatile component/analyte, which is located adjacent to said collection site, such that liquid sample from which has been evaporated volatile/semivolatile component/analyte, which accumulates in said collection site, can exit therethrough in use. The present invention fractional-volatilization separator system further comprises a means for entering a flow of carrier gas located vertically between the location at which said vertically lower extents of said outer envelope and said surface area providing essentially convex protrusion are essentially continuous, and the vertically superior location of said liquid sample inlet means, and further comprises means for allowing entered carrier gas to exit said fractional-volatilization separator system located vertically above the location of said means for entering a flow of carrier gas. In use, evaporated volatile/semi-volatile component/analyte which evaporates from said liquid component/analyte containing sample is caused to accompany said carrier gas out of said means for allowing said entered carrier gas to exit said fractional-volatilization separator system and said liquid sample from which has been evaporated said volatile/semi-volatile component/analyte is caused to exit via said means for quickly removing liquid sample. The end result being the providing of separated volatile/semi-volatile component/analyte, and liquid sample from which has been evaporated said volatile/semi-volatile component/analyte.

Continuing, a method of separating volatile component/analyte present in a liquid component/analyte containing solution from said liquid component/analyte containing sample solution comprises the steps of:

a. providing a fractional-volatilization separator system as described infra;

b. entering a liquid component(s)/analyte(s) containing sample solution thereto by way of said liquid sample inlet means, or by way of a sample delivery means positioned within in a liquid sample inlet means guide means;

c. optionally controlling the temperature of said surface area of said elongated surface area providing essentially convex protrusion to cause selective component/analyte evaporation from said liquid component/analyte containing sample solution;

d. entering a carrier gas to said means for entering a flow of carrier gas;

e. accessing said separated volatile component(s:)/analyte(s) at said means for allowing said entered carrier gas to exit said fractional-volatilization separator system; and f. continuously causing "spent", "residual", "concentrated", "enriched" or "purified" liquid sample solution from which volatile component(s)/analyte(s) have/has been removed, (evaporated), and which has reached the collection site located where said fractional-volatilization separator system elongated dimension outer envelope and said elongated surface area providing essentially convex protrusion are essentially continuous, to be quickly and immediately removed via said means for quickly removing liquid sample from which has been evaporated volatile component(s:)/analyte(:s).

It is to be understood that the present invention fractional-volatilization separator system can be equally applied to analytical tasks and to industrial scale tasks. Analytical tasks include the production of mercury vapor from a mercury component/analyte containing sample solution which has been premixed with stannous chloride, (or other chemical reductant), which mercury vapor is then, for instance, caused to enter a Normal or Long-Path Ultra Violet Absorbance Cell for detection and determination of the concentration thereof. Another analytical task involves the evaporation of solvent vapor from solutions of non-volatile analytes to effect pre-concentrated sample solutions prior to entry thereof into analytical instruments which determine their concentration, such as inductively couple plasma based systems and mass-spectrometer based systems. Another usage involves the selective production of organo-metallic or organo-analyte vapors from an organo-metallic or organo-liquid sample mixture or solution, which organic or organo-metallic vapors are then removed with the carrier gas, and for instance, caused to enter a normal or long-path infrared optical absorbance cell for detection and determination of the concentration thereof by infrared, infrared Fourier Transform, and/or mass spectrometry, spectrophotometry or spectroscopy. Such usage includes the evaporation and detection of volatile or semivolatile organic carbon present in liquid sample solutions. Industrial scale component/analyte separation include distillation processes which serve to remove volatile mixture components or contaminates from a liquid, and evaporation processes for distilling, purifying, concentrating or desalinating liquids. In addition, it is mentioned that evaporative cooling procedures can be effected by proper utilization of a larger scale present invention system.

It is to be especially appreciated that the stable continuous action enabled by the present invention, along with the fast wash-out time between samples, (performed when samples are changed), greatly enhances analytical, as well as industrial applications.

The present invention fractional-volatilization separator system will be better understood by reference to the Detailed description Section of this Disclosure with reference being had to the accompanying Drawings.

SUMMARY OF THE INVENTION

It is a general purpose of the present invention to provide a fractional-volatilization separator system which can, but need not necessarily, be of simple, rigid, one piece construction, which is easy to manufacture, which provides a wettable sample component(s:)/analyte(s) evaporation surface area, which optionally allows highly efficient and accurate internal temperature control, which allows continuous operation, which provides smooth and stable flow of sample component(s)/analyte(s) vapors over time, which is quick and easy too wash-out between samples, which stabilizes and responds quickly to new sample, (following sample change), which enhances detection of trace amounts of sample component(s)/analyte(s), and which is conducive to enhanced repeatability and accuracy of analytical instruments with which said fractional-volatilization separator is used.

It is primary purpose of the present invention too provide a fractional-volatilization separator system which allows high vapor enrichment and trace-component(s)/analyte(s) sensitivity of volatile components/analytes at a vapor exit location and recovery of highly concentrated, "enriched", purified, non-volatile component(s)/analyte(s) at a liquid exit location.

It is another purpose of the present invention to provide a fractional-volatilization separator system which allows good thermal isolation of an evaporation effecting surface area so that environmental effects thereupon are minimized.

It is yet another purpose of the present invention to provide an efficient fast responding fractional-volatilization separator system which does not require carrier gas bubbling-action.

It is still yet another purpose of the present invention to provide a fractional-volatilization separator system which does not impose hydraulic transients or fluctuations on a gas stream in use.

It is yet still another purpose of the present invention to provide a fractional-volatilization separator system which is not subject to temporal variations in liquid surface-area/volume ratio in use.

It is still another purpose of the present invention to provide a fractional-volatilization separator system which does not induce foaming or frothing in liquid component(s)/analyte(s) containing sample in use.

It is still yet another purpose yet of the present invention to, provide a fractional-volatilization separator system which minimizes instability and uncertainty in analytical detector response and reduces the complexity of system calibration in use.

It is another purpose of the present invention too provide a fractional-volatilization separator system which allows unusually quick and easy wash-out between samples.

It is yet another purpose of the present invention to provide a fractional-volatilization separator system which serves simultaneously to stabilize the liquid sample boundary perimeter, liquid sample surface area, liquid sample contained component(s)/analyte(s) volatilization rate, gas-phase enrichment factor and analytical detector response in use.

It is yet still another purpose of the present invention to provide a system which minimizes the liquid sample boundary perimeter, while maximizing the exposed evaporation surface area of the liquid sample.

It is still yet another purpose of the present invention to provide a fractional-volatilization separator system which maximizes static liquid component(s)/analyte(s) containing sample surface area and minimizes liquid sample volume and vapor headspace volume.

It is yet still another purpose of the present invention to provide a fractional-volatilization separator system which allows smooth, continuous, unbroken, non-bubbling, non-pulsatile, non-fluctuating liquid component(s)/analyte(s:) containing sample through flow.

BRIEF DESCRIPTION OF THE DRAWINGS

FIG. 5a1 shows a cross-section side elevational view of a preferred embodiment of the present invention fractional-volatilization separator system comprising a fixed liquid sample inlet means.

FIG. 5a2 shows a cross-section side elevational view of a preferred embodiment of the present invention fractional-volatilization separator system comprising a liquid sample inlet guide means for securing a variable position liquid sample delivery means in use.

FIGS. 5a3–5a16 show variations on system geometry which are within the scope of the present invention fractional-volatilization separator system.

FIG. 5b1 shows a cross-section side elevational view of an insertable liquid sample delivery means for use in the embodiment of the present invention fractional-volatilization separator system shown in FIG. 5a2.

FIG. 5b2 shows a cross-sectional side elevational view of an alternative insertable liquid sample delivery means for use in the embodiment of the present invention fractional-volatilization separator system shown in FIG. 5a2.

FIG. 5b3 shows a cross-sectional side elevational view of a second embodiment of an insertable liquid sample delivery means for use in the embodiment of the present invention fractional-volatilization separator system shown in FIG. 5a2.

FIGS. 6f–6aa show various, non-limiting, shapes for the surface area providing essentially convex protrusion and/or outer envelope of the present invention, which shapes are non-limiting examples of shapes within the scope of the present invention fractional-volatilization separator system.

FIGS. 10a, 10b 10c show, graphically presented, typical results obtained by use of the present invention fractional-volatilization separator system when utilized in various "accelerated throughout" modes.

DETAILED DESCRIPTION

Figure 1:
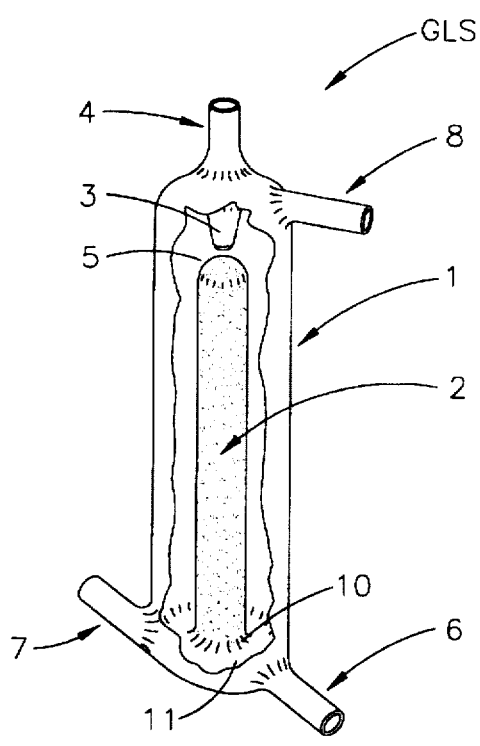
FIG. 1. shows a partially cut-away perspective view of a preferred embodiment of the present invention fractional-volatilization separator system.
Figure 2:
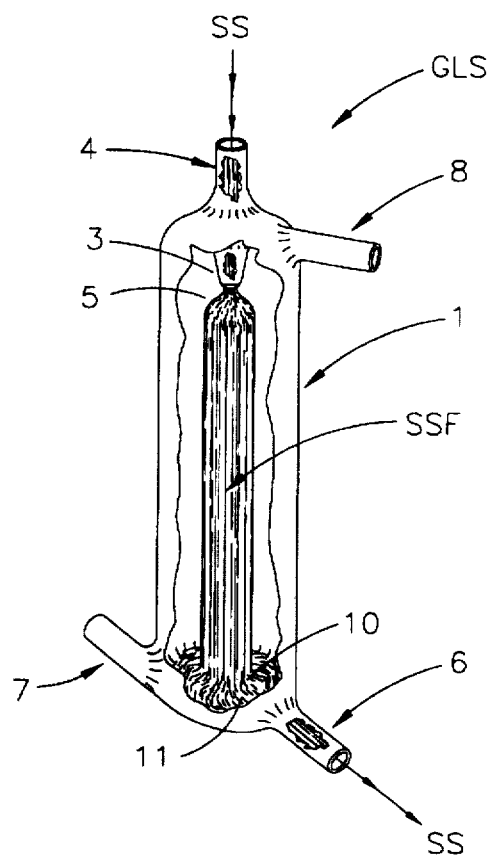
FIG. 2 shows a partial cut-away perspective view of a preferred embodiment of the present invention fractional-volatilization separator system, with liquid component/analyte containing sample entered at a liquid sample inlet means for entering component/analyte containing sample, then flowing as a film over a surface area providing convex protrusion therein, and out of a means for quickly removing liquid sample.
Figure 3:
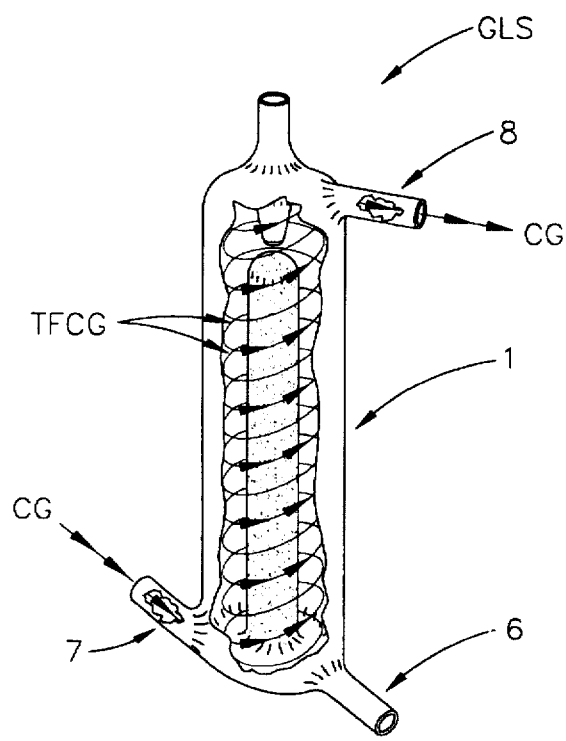
FIG. 3 shows a partial cut-away perspective view of a preferred embodiment of the present invention fractional-volatilization separator system, with a tangentially oriented counter spiral carrier gas flow proceeding therethrough, said tangentially oriented counter spiral carrier gas flow having been entered at a means for entering carrier gas, and allowed to exit at a means for allowing entered carrier gas too exit.

Turning now to the drawings, there are shown in FIGS. 1 through 3 partially cut-away perspective views of the system if a preferred embodiment if the present invention Fractional-Volatilization Separator System (GLS). Shown are an Outer Envelope (1) presenting with a preferred, Elongated Dimension.

Figure 6A:
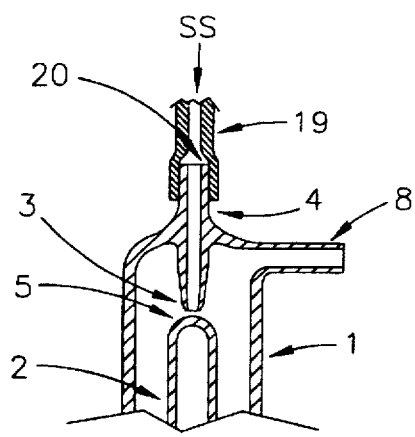
FIG. 6a shows a partial cross-section side elevational view of the preferred embodiment of the present invention fractional-volatilization separator system shown in FIG. 5a1 showing a liquid sample inlet means with a flexible delivery hose affixed thereto.
Figure 6B:
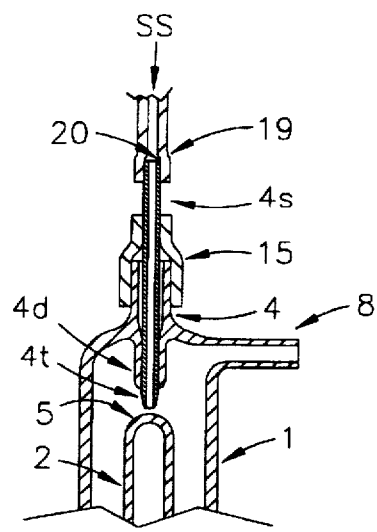
FIG. 6b shows a partial cross-section side elevational view of the preferred embodiment of the present invention fractional-volatilization separator system with a sample delivery means of FIG. 5b1 positioned in the liquid sample inlet means :if the FIG. 5a2 embodiment, in combination with a position securing means and including a flexible delivery hose.
Figure 6C:
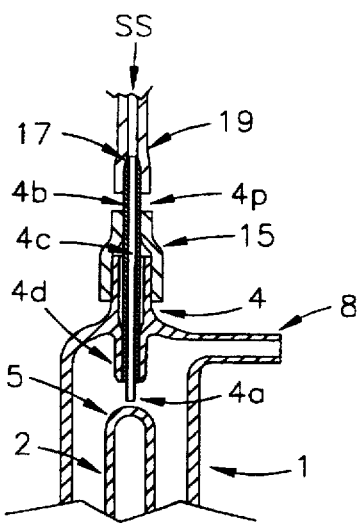
FIG. 6c shows a partial cross-section side elevational view of the preferred embodiment if the present invention fractional-volatilization separator system with a sample delivery means of FIG. 5b2 positioned in the liquid sample inlet guide means of the FIG. 5a2 embodiment, in combination with a position securing means, and a flexible delivery hose.
Figure 6D:
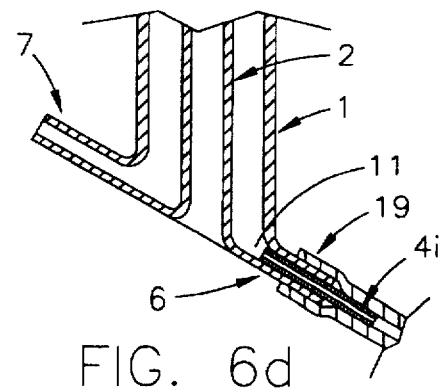
FIG. 6d shows a partial cross-section side elevational view of a preferred embodiment of the present invention fractional volatilization separator system, as shown in FIGS. 5a1 and 5a2, with an inner diameter restricting insert positioned in a means for removing liquid sample thereof, in combination with a position securing means/flexible drainage hose.

Within a space concentrically defined by said Outer Envelope (1) is present an upward protruding, Surface Area Providing Essentially Convex Protrusion (2), which is also preferably Elongated. It is to be understood that the Outer Envelope (1) and Surface Area Providing Essentially Convex Protrusion (2) of the present invention can, in various embodiments, comprise essentially rod, essentially sharpened pencil, essentially blunt pencil, essentially closed top cylinder, essentially spherical, essentially hemispherical, essentially pyramidal, essentially Washington Monument shape, essentially closed top hour-glass, essentially closed top multiple repeating hour-glass, essentially conical, essentially bullet, essentially helical screw-thread and other functional shapes, including any combinations thereof, with essentially rounded, essentially conical, essentially bullet-shaped, essentially nippled or other functional shaped apex region, in addition too, or instead of being elongated, and such alternative functional embodiments are within the scope of the present invention. The requirement being only that the surface area providing protrusion is substantially essentially convex, has a closed apex, (eg. said apex has no holes, or slots and the like present therethrough), and in use receives a liquid applied too said apex thereof. It is further disclosed that any Functional Surface Area Providing Essentially Convex Protrusion Shape can include a small Flat Region at the upper extent thereof. FIGS. 6f through 6aa demonstrate various non-limiting possible shapes for the Surface Area Providing Essentially Convex protrusion (2), and for the Outer Envelope.

Figure 4:
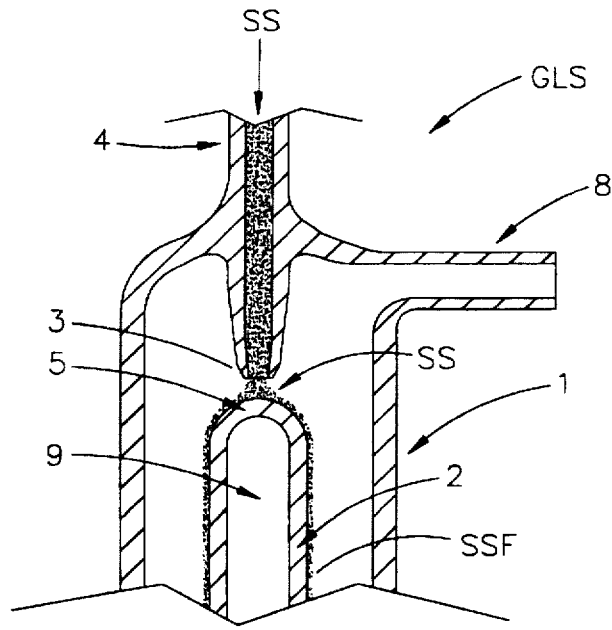
FIG. 4 shows a cross-section side elevational view of a preferred embodiment of the present invention fractional-volatilization separator system embodiment, showing in enlarged cross-section, liquid component/analyte containing sample being entered thereto, at a liquid sample inlet means and flowing onto a surface area providing essentially convex protrusion, upon which surface area is formed a film of said liquid component/analyte containing sample.

Continuing, it is to be noted that the Surface of each shown Elongated Surface Area Providing Essentially convex Protrusions (2) has, in FIGS. 1 and 3, many dots present thereon. This is to signify that said Surface is preferably of a composition, and/or treated and/or textured so as to be phillic, easily wettable, and appropriate to readily form a Liquid Component/Analyte Containing Sample Solution Film (SSF) thereupon in use. There is also shown a Fixed Location Liquid Sample Inlet Means (4) for introducing Liquid Component/Analyte Containing Sample Solution (SS:) to said present invention Fractional-Volatilization Separator System (GLS:) in use. FIG. 2 shows Liquid component/Analyte containing Sample Solution (SS) entered to the present invention Fractional-Volatilization Separator System (GLS), is present as a Film (SSF) evenly distributed over the Surface Area of said Elongated Surface Area Providing Essentially Convex Protrusion (2). It should be appreciated that the entered Liquid component/Analyte containing Sample Solution (SS:) is caused to flow, and spread, under the influence of gravity, over the upward facing Apex (5:) of said Elongated Surface Area Providing Essentially Convex Protrusion (2):. FIG. 4 shows a partial cross-section elevational view of said Liquid Component/Analyte Containing Sample Solution (SS:) being entered via said Fixed Location Liquid Sample Inlet Means (4:) Note that the liquid Dispensing Tip (3:) of said Fixed Location Liquid Sample Inlet Means (4) is situated essentially centrally with respect to, and situated in close vertical proximity to, the Apex (5) of said Elongated Surface Area Providing Essentially Convex Protrusion (2), said vertical proximity requirement being appropriate to produce a continuous, unbroken stream of said Liquid component Analyte containing Sample Solution (SS) between said Dispensing Tip (3:) and said Apex (5) under conditions determined in view of said dispensing tip inner diameter (i.d.), a Liquid Component/Analyte Containing Sample Solution (SS) temperature and surface tension and desired Dispensing Rate of said Liquid Component/Analyte Containing Sample Solution (SS). For Analytical measurements involving mercury as an Analyte in a room temperature Liquid Component/Analyte Containing Sample Solution (SS), this distance is typically on the order of one-half (0.5) millimeter, (with a typical, but not limiting, range being 0.2 to 0.8 millimeter where the liquid is water, or a water based solution, (but not limited thereto)), and an ideal dispensing rate of four (4) milli-liters/minute, (within the typical range range if one-half (0.5) to ten (10) mL/min, but not limited thereto), is utilized. Also, the dispensing tip is typically, but nct limited to 0.9 mm i.d. Said conditions typically provide that entering Liquid component/Analyte Containing Sample Solution (SS) is continuously evenly dispensed, spread to and distributed in a continuous unbroken stream over the Surface Area provided by said Elongated Surface Area Providing Essentially Convex Protrusion (2), as demonstrated by FIG. 2. Note also that a Means For quickly Removing ("Residual", "Spent", "Purified", "Concentrated", "Enriched") Liquid Sample (6), from which has been evaporated Volatile Component/Analyte; or for removing "Concentrated" Sample Solution, from which has been evaporated Volatile Component/Analyte, (eg. remaining concentrated salt solution after substantial water has been evaporated therefrom), is shown located in said preferred embodiment of the present invention Fractional-Volatilization Separator System (GLS), at a position within the locus (10) whereat said Elongated Dimension Outer Envelope (1), and said Elongated Surface Area Providing Essentially convex Protrusion (2) are essentially continuous, (see region identified by (10) & (11). In use, Liquid Component/Analyte Containing Sample Solution (SS) from which has been evaporated volatile Component/Analyte, which arrives at a Collection Site (11) location, which Collection Site (11) location is continuous with said Means For Removing Liquid Sample (6), is quickly removed through said Means For Removing Liquid Sample (6). This prevents accumulation thereof and "Flooding" of the Surface Area provided by said Elongated Surface Area Providing Essentially Convex Protrusion (2), prevents Carrier Gas from "Bubbiing" through (SS), promotes smooth continuous operation of the present invention Fractional-Volatilization Separator System, and provides rapid draining and washout between Different Liquids or liquid Component/Analyte Containing Sample Solutions which might be sequentially entered thereto.

Turning now to FIG. 3, there is shown a Means For Entering Carrier n as (CG), identified by numeral (7). Also shown is a Means For Allowing Said Entered Carrier Gas To Exit said present invention Fractional-Volatilization Separator System (GLS), identified by numeral (B). Note that said Carrier gas (CG) flow through said Fractional-Volatilization Separator System (GLS) is shown, in the preferred embodiment, as providing a Tangentially Oriented Counter, (to the Liquid Sample flow direction), Spiral Flow Locus identified as (TFCb). In use said Tangentially Oriented Counter Spiral Flow of Carrier Gas (TFCG) serves to sweep, or propel, Evaporated Component (s) Analyte (s) evaporated from the (SSF), (shown entered to the Fractional-Volatilization Separator System (GLS) in FIGS. 2 and 4 as (SS)), present in said Film (SSF) on said Essentially Convex Protrusion (2), through said preferred embodiment of said present invention Fractional -Volatilization Separator System (GLS), and out of said Means For Allowing Said Entered Carrier Gas to exit said preferred embodiment of said present invention Fractional-Volatilization Separator System (GLS), identified by numeral (8). (Note that other Carrier Gas Flow loci, such is Vortex or Laminar flow, are also within the scope of the present invention). It is also noted that said Means For Allowing Entered Carrier Gas to Exit (8) is located near the Liquid Sample Inlet Means (4). It is preferred, but not required, that said Means For Allowing Said Entered Carrier Gas to Exit (8) be located at or above sixty (60%) percent, (preferably eighty (8%) percent and higher), of the length of said Essentially Convex Protrusion (2), as measured from the location at which said Outer Envelope (1) and Said Essentially Convex Protrusion (2) are essentially continuous, at the location at which said Means For Removing Liquid Sample (6) is present, (but not necessarily in a common vertical plane therewith). It should be appreciated that the Means For Entering Carrier Gas (CG), identified by numeral (7), is preferably located slightly vertically superior to the Means For Removing Liquid Sample (6). However, this is not an absolute requirement of the present invention Fractional-Volatilization Separator System, because in use, Liquid Sample Analyte/ Component Containing Solution (SS) from which has been evaporated Volatile or Semivolatile Component/Analyte, and which arrives at a Collection Site (11) location, is, while still essentially in a "Film" geometry at Collection Site (11), quickly and immediately collected and removed, and abruptly transformed from a film geometry to a bulk tubular flow geometry, via said Means For Quickly Removing Liquid Sample (6). An important point is that in system described, Carrier Gas need not "Bubble" or otherwise proceed through liquid sample solution (SS) bulk from which has been evaporated Volatile or Semivolatile Analyte/ Component to proceed in a Tangentially Oriented Counter Spiral Flow Locus (TFCG), (or other locus such as Laminar), upward and out of said Means For Allowing Said Entered Carrier Gas to exit said present invention Fractional-Volatilization Separator System (GLS) , identified by numeral (8). Thus, with the exception of FIG. 5a10 (a no-preferred embodiment), all bubbling action can be eliminated from the preferred embodiment of the present invention in use.

FIG. 4 also shows that the Elongated Surface Area Providing Essentially Convex Fractional (2) can comprise, in a preferred embodiment, a Hollow Space (9) which is accessible from the bottom, (see FIGS. 5a and 5a2), of the present invention Fractional-Volatilization Separator System (GLS). Said hollow space can occupy a majority of the space internal to the outer wall of said Essentially Convex Protrusion (2), or can occupy only a portion thereof. In use, a Temperature Control, (ie. Heating, Cooling, Stabilizing, Insulating), Means, can optionally be placed into, a present Hollow Space (9), effectively contact an inner concave howwlo space wall if said Essentially Convex, Protrusion (2), and be utilized to precisely control the temperature of the (SSF) contacting Outer Surface Area provided by said Elongated Surface Area Providing Essentially Convex Protrusion (2). As well, said Hollow Space (9) can be plugged, sealed or filled with an insulating material or with a heat transfer medium such as a gas, liquid, paste or gel etc., and heating, or cooling, or temperature stabilization, of the Surface Area of said Surface Area Providing Essentially Convex Protrusion (2) optionally provided via said gas, liquid or paste or gel etc. acting as a heat transfer (contact) medium between said elongated Surface Area Providing Essentially Convex Protrusion (2) and an optional external heating or cooling or temperature regulation means immersed therein or in contact therewith. (Note, said Temperature control means should be understood as co-represented by identifier (9), as appropriate).

FIG. 5a shows a cross-section side elevational view of a preferred embodiment of the present invention Fractional-Volatilization Separator, or Gas-Liquid Separator (GLS) System. In this embodiment one-piece construction, (typically, but not necessarily, of glass material), is employed, and the liquid dispensing tip (3) of the essentially vertically oriented Fixed Location Liquid Sample Inlet Means (4) is at a fixed gap distance above the Apex (5) of the essentially vertically oriented Surface Area Providing Essentially Convex Protrusion (2). In particular, note that the Means For Receiving Liquid Sample (6) is shown as being at a slightly lower vertical level than is the Means For Entering Carrier Gas (7) and that both the Means For Removing Liquid Sample (6) and the Means For Entering Carrier Gas (7) are shown to project from the essentially vertically oriented Outer Envelope (1), at an angle which is between horizontal and vertical. The FIGS. show the difference in vertical location between the Means For Removing Liquid Sample (6) and the Means For Entering Carrier Gas (7) as effected by a sloping base prevent carrier gas (CG) bubbling and designed to promote rapid liquid (SS) drainage, but it is to be understood that such could be effected by a "stepped" geometry, (see FIGS. 5a7 and 5a8). Again, this is effective in preventing "Bubbling" and "Frothing" or "Foaming" related problems, which can be significant in existing known systems, such as identified in the Background Section in this Disclosure. In particular, any Liquid reaching a single, focused lower extent located Collection Means (11), which is continuous with the Means For Quickly Removing Liquid Sample (6) in all FIGS., (except FIGS. 5a9 and 5a10 ), will be encouraged to exit the Fractional-Volatization Separator system, at a level vertically below that at which Carrier Gas is entered via Means For Entering Carrier Gas (7). This, it will be appreciated, in addition to, essential elimination of Bubbling and Frothing and Foaming effects, serves as well as to facilitate rapid wash-out, and ease in wash-out of the present invention Fractional-Volatization Separator system, because Liquid Sample Solution reaching the Collection Means (11) region of the present invention Fractional-Volatilization Separator is not allowed to accumulate therein, in all FIGS. except FIG. 5a10). Also shown in FIG. 5a1 is the Means For Allowing Said Entered Carrier Gas To Exit (8), projecting essentially horizontally at the (GLS upper extent. Note that said Means For Allowing Said Entered Carrier Gas To Exit (8) is adjacent to, and oriented at essentially ninety (90) degrees with respect to, said Fixed Location Liquid Sample Inlet Means (4). This is a preferred arrangement, however, said Means For Allowing Said Entered Carrier Gas To Exit (8) (8') can be located at a lower or higher respective vertical position with respect to said Liquid Sample Inlet Means (4) (4'), (see FIGS. 5a4–5a6 where (8') is higher than (4') and FIG. 5a3 where (8') is lowered in non-preferred embodiments), and be within the scope of the present invention.

FIG. 5a2 shows a cross-section side elevational view of a modified preferred embodiment of the present invention Fractional-Volatilization Separator, or, alternatively titled, Gas-Liquid Separator (GLS) System. Said FIG. 5a2 embodiment is essentially similar to the embodiment of FIG. 5a1, with the exception that the vertically oriented Liquid Sample Inlet Means (4) for entering Li quid Sample Solution (SS) functions as a guide (4), (also identified as (4d) at a lower extent thereof), within which a Separate Slidably Positioned Liquid Sample Delivery Means, (see FIGS. 5b1, 5b2 and 5b3), can be positioned in use. It is to be appreciated that the identifier (4) is utilized to identify a Stationary Liquid Sample Inlet Means in FIG. 6a and to identify a similarly situated Guide Means into which a Slidably Mounted Separate Liquid Sample Delivery Means (4s) with Dispensing Tip (4t), (see FIGS. 5b1 and 6b), or Slidably Mounted Liquid Sample Delivery Means (4p) or (4q) with Dispensing Tip (4a) (see FIGS. 5b2 6c, and 6e), can be Slidably Position in use, as all three said structures are essentially similar and similarly located. Note, however, that said Liquid Sample Inlet Guide Means identified by numeral (4) is shown as being of a larger inner diameter at its upper aspect than at its lower aspect (4d). This is a result Liquid typical manufacturing glass blowing techniques involving precision inner diameter, (i.d), bore tubing required in the lower aspect liquid inlet guide (4d) only, and when present Also provides a convenient means for easing entry of insertion of a Slidably Positioned Liquid Sample Delivery Means as shown in FIGS. 5b1, 5b2 and 5b3. (Note that FIGS. 6a, for instance, does not show such a diameter reduction of the Liquid Sample Inlet Guide Means (4) between upper (4) and lower (4d) extents thereof and are within the scope of the present invention. See also FIGS. 5a/15 and 5a16). Also shown in FIG. 5a2. is the Means For Allowing Said Entered Carrier Gas To Exit (8), projecting essentially horizontally at the (GLS) upper extent. Note that said Means For Allowing Said Entered Carrier Gas To Exit (8) is adjacent to, and oriented at essentially ninety (90) degrees with respect to, said Liquid Sample Inlet Guide Means (4:) &. (4d). The Means For Removing Liquid Sample (6) and said Means For Entering Carrier Gas (7) are shown essentially as described with respect to FIG. 5a1.

Again, it is to be noted that FIGS. 5a1 and 5a2 show that the Means For Entering Carrier Gas (7) is located at a vertically superior position to the Means For Quickly Removing Liquid Sample (6) by means of an essentially constant "sloping base" therebetween along the lower aspects of said Outer Envelope (1) and said Essentially Convex protrusion (2) along the locus whereat said Outer Envelope (1) and said Essentially Convex Protrusion (2) are essentially continuous, (see (10) in FIGS. 1 and 2). It is to be understood that this is exemplary rather than limiting and that said relative positioning could be embodied by other than a gradual slope, (eg. see FIGS. 5a7 and 5a8 for a "step" embodiment), or the change in relative vertical positioning can be absent, (see FIG. 5a9), or the a step can be oppositely directed, (see FIG. 5a10), and the resulting embodiments, though not necessarily preferred, are within the scope if the present invention. In particular, FIG. 5a10 will accumulate liquid sample and carrier will bubble therethrough in use. It is also to be understood that the Means For Allowing Carrier Gas To Exit (8) is preferably functionally vertically positioned present between said Means For Entering Carrier Gas (7) and said Liquid Sample Inlet Means or Liquid Sample Inlet Guide Means identified by numeral (4) in FIGS. 1–6e. Typically, though not necessarily, said Means For Allowing Carrier Gas To Exit (8) is positioned to project from said Outer Envelope (1) at a vertical level between that of said apex (5) of said Essentially Convex Protrusion (2) and the point at which said Liquid Sample Entering Means (4) or Liquid Sample Entering Guide Means (4) enters the essentially closed upper aspect of said Outer Envelope (2), however, a vertical level in excess of sixty (60%) percent, (preferrably in excess of eighty (80%) percent), the length of the Essentially Convex Protrusion (2) above the location at which the lower extents of said Outer Envelope (1) and said Essentially Convex Protrusion (2) are continuous at the location of the Means For Quickly Removing Liquid Sample (6) is a more general guideline. It is also noted that said Means For Allowing Carrier Gas To Exit (8) is typically, though not necessarily, positioned to project from said Outer Envelope (1) at a location on said Outer Envelope (1) laterally opposed to said Means For Entering Carrier Gas (7), as is said Means For Quickly Removing Liquid Sample (6). This is shown in FIGS. 5a1 and 5a2. It is further noted that said Means For Entering Carrier Gas (7), and/or said Means For Allowing Carrier Gas To Exit (B), and/or said Means For Quickly, Removing Liquid Sample (6) need not be in a common plane, but rather each can be positioned at an angle, which, viewed from above, are in common, or other than common planes. It is also noted that FIGS. 5a1 and 5a2 show present invention embodiments with the elements (1), (2) (3), (4), (4d), (5), (6), (7), (8) and (9) thereof in typical realistic relative proportions to one another. (See the Disclosure Section for numerical measurement dimensions of a typical present invention Fractional-Volatilization Separator (GLS) utilized in analytical chemistry applications).

Figure 6E:
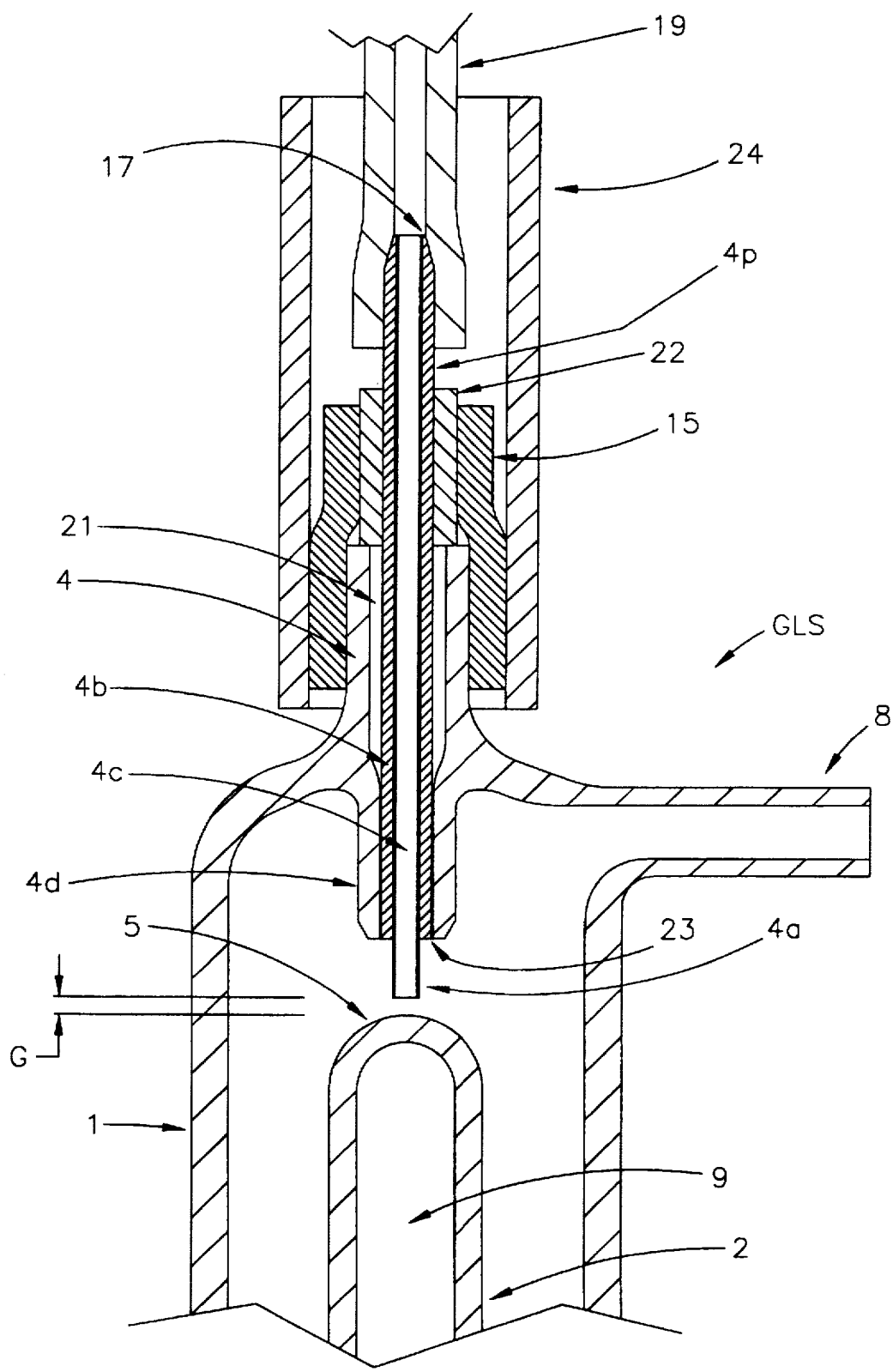
FIG. 6e shows an expanded scale side elevational view of a FIG. 5a2 preferred embodiment of the present invention fractional-volatilization separator system, showing a FIG. 5b2 sample delivery means with a stress relieving means and a sample delivery means positioning means in place thereon.
Figure 6F:
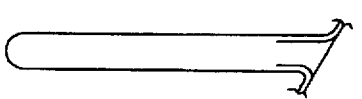
Figure 6G:
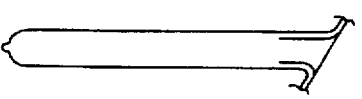
Figure 6H:
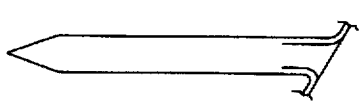
Figure 6I:
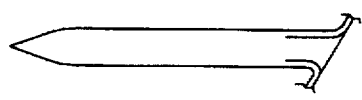
Figure 6J:
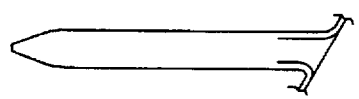
Figure 6K:
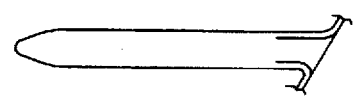
Figure 6L:
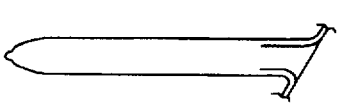
Figure 6M:
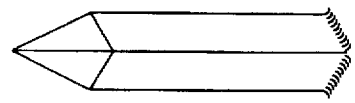
Figure 7:
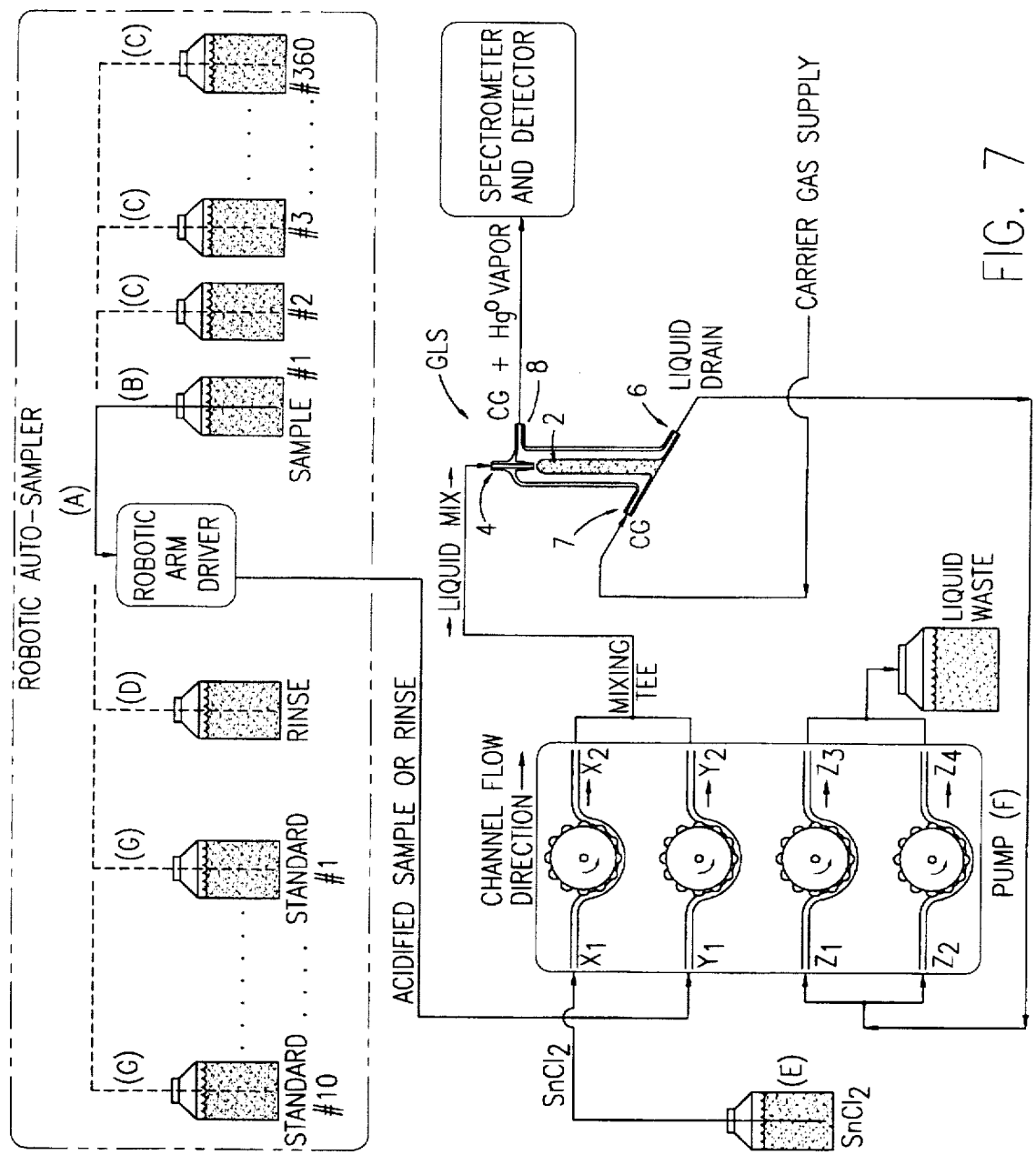
FIG. 7 shows a typical system in which the present invention fractional-volatilization separator system is utilized. Said system is an exemplary, non-limiting, configuration used in the detection of mercury.
Figure 8:
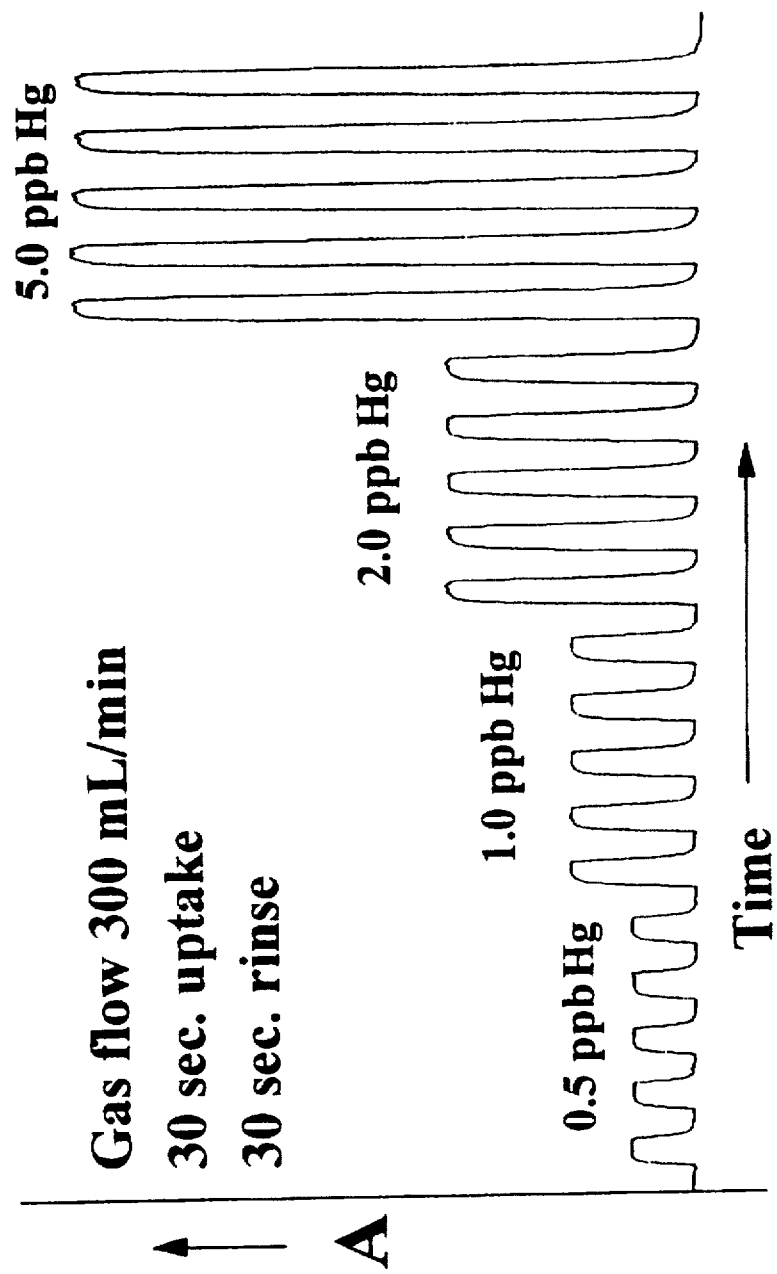
FIG. 8 shows, graphically presented, typical calibration results obtained by use of the present invention fractional-volatilization separator system when utilized in a "normal-throughput" mode, (for analytical determination of mercury presence in drinking water).
Figure 9:
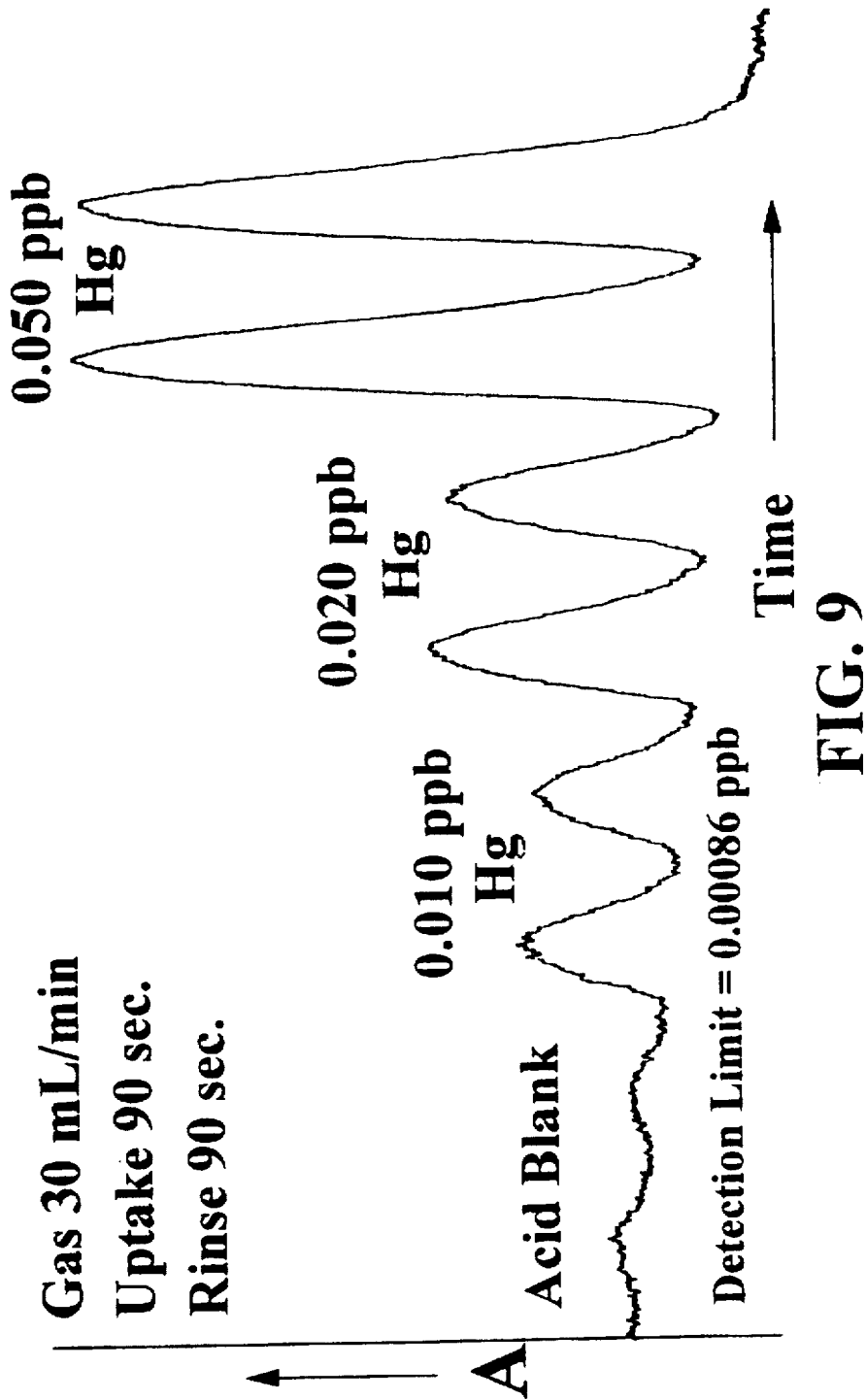
FIG. 9 shows, graphically presented, typical results obtained by use of the present invention fractional-volatilization separator system when utilized in a "high sensitivity" , (mode for determination of mercury in very low concentrations).

FIGS. 5a3 through 5a16 show less preferred variations on the described present invention Fractional-Volatization Separator System (GLS) system which are too be considered within the scope thereof. It is to be understood that Primes "'" are utilized with system element identifying Numerals in said Figures to indicate a geometrical difference as compared to analogically similar elements in the preferred embodiments shown in FIGS. 1 through 6e. In particular note that FIG. 5a4 provides the Means For Allowing Carrier Gas To Exit (8') at a vertical location above that shown for the Means For Allowing Carrier Gas To Exit (8) in FIGS. 1 through 6e and above the Liquid Sample Entry Means (4') of said FIG. 5a4. Also note that FIGS. 5a4–5a6 provide the Means For Allowing Carrier Gas To Exit (8') at the uppermost extent if the Fractional-Volatization Separator System (GLS), with the Liquid Sample Entry Means (4') provided through the Outer Envelope (1) thereof at a vertical location between the lower extents of said Outer Envelope (1) and Essentially Convex Protrusion (2) whereat they are continuous, (as identified by the Numeral (10) in FIGS. 1 through 6e), and said upper extent of said Outer Envelope (1) of said Fractional-Volatization Separator System (GLS). FIGS. 5a7–5a11 show variations on the Means For Entering Carrier Gas entry (7') in relation to the Means For Quickly Removing Liquid Sample (6') and (6) as the case might be. FIG. 5a7 and 5a8 shows the Means For Entering Carrier Gas entry (7') at a higher location than Means For Quickly Removing Liquid Sample (6) and (6') respectively, with said vertical level change being by way of a "step", rather than a "slope" as shown in FIGS. 1 through 6e. FIG. 5a9 shows the Means For Entering Carrier Gas entry (7') and the Means For Quickly Removing Liquid Sample (6') at essentially equivalent levels and FIG. 5a10 shows the Means For Quickly Removing Liquid Sample (6') at a vertical level above the Means For Entering Carrier Gas entry (7'). The FIG. 5a10 embodiment, it is noted, is particularly not preferred. FIGS. 5a11–5a14 show variations of the Means For Entering Carrier Gas (7'). In FIG. 5a11 said Means For Entering Carrier Gas (7') is located non-preferred at a higher vertical level as compared to embodiments shown in FIGS. 1 through 6e. FIGS. 5a12–5a14 show the Means For Entering Carrier Gas (7') is present through a wall in an at least a partially hollow (9) Essentially Convex Protrusion (2). The FIGS. 5a12 and 5a13 embodiments provide for a pressurization of an essentially hollow (9) volume of the Essentially Convex Protrusion (2), with entry of Carrier Has being "tangentially into the page" and "to the left" respectively, as shown. FIG. 5a14 show the Means For Entering Carrier Has (7') is present through a wall in an at least a partially hollow (9) Essentially Convex Protrusion (2), but said embodiment provides for access to the hollow (9) portion of said Essentially Convex Protrusion (2). In addition, note that FIGS. 5a15 and 5a16 show an embodiment of the present invention Fractional-Volatization Separator System (GLS) in which the upper extent of Liquid Sample Inlet Guide Means (4) is of the same inner diameter as the lower extent thereof identified as (4d), (note this is in contrast to the embodiments shown in FIGS. 6b, 6c and 6e. That is, in FIGS. 5a15 and 5a16 there is no area (21) present, (as identified by (21)

in FIG. 6e). Again, the system geometries shown in FIGS. 5a3 through 5a16 are within the scope of the present invention, but are not necessarily preferred embodiments.

FIG. 5b1 shows a cross-section side elevational view of a Separate Slidably Positioned Liquid Sample Delivery Means (4s), with a Dispensing Tip (4t), and FIGS. 5b2 and 5b3 show Alternative Separate Slidably Positioned Liquid Sample Delivery Means (4p) (4q) and Dispensing Tip (4a) which is comprised of a thin walled, small inner diameter Inner Sample Delivery Tube (4c) present within a concentrically surrounding Protective Outer Jacket (4b) In the preferred embodiment, said small inner diameter Inner Sample Delivery Tube (4c) is constructed of thin-walled quartz or glass "Capillary" tubing and projects a bit beyond the protective Outer Jacket (4b) to, form a Dispensing Tip identified as (4a) in FIG. 5b2 and 5b3. Said Protective Outer Jacket (4b) is typically composed of a material which is heat-shrinkable, such as Teflon. Said Protective Outer Jacket (4b) serves to protect the major extent of said thin-walled Inner Sample Delivery Tube (4c), and when the FIG. 5b2 or 5b3 embodiment of the Separate Slidably Positioned Liquid Sample Delivery Means (4p) is slid into the FIG. 5a2 Guide Means identified as (4) and (4d), it serves to effect a "Slip-Fit", or Carrier Gas-Tight "Press-Fit" with said Guide Means (4d). Note that Securing Means (15) and flexible elastic Sample Delivery Hose (19), as shown in FIGS. 6b and 6c, can also be utilized to further effect a Gas-Tight "Slip-Fit", or "Press-fit" between said Guide Means (4d) and said Protective Outer Jacket (4b).

FIG. 6a shows the upper aspect of a present invention Fractional-Volatization Separator System (GLS) which comprises a Fixed Position Liquid Sample Inlet Means (4) with Dispensing Tip (3), as also shown in FIG. 5a1. Also shown is a flexible Delivery Hose (19) means of securing a source of Liquid Sample Solution (SS) to said Liquid Sample Inlet Means (4). Said flexible Delivery Hose (19) is typically composed of elastic material such as viton, silicone or other organo-polymer tubing. The inner diameter of Securing Means lowermost extent of said elastic Sample Delivery hose (19) is slid over the outer diameter of Liquid Sample Inlet Means (4) to provide a liquid-tight seal in the region (20).

FIG. 6b shows the upper aspect of a present invention Fractional-Volatization Separator System (GLS) such as shown in FIG. 5a2, comprising an Adjustable Position Liquid Sample Delivery Means (4s) with Dispensing Tip (4t), (as shown in FIG. 5b1), which has been vertically slid into the upper aspect of the Elongated Dimension Outer Envelope (1) Liquid Sample Inlet Guide Means (4) (4d) so as to orient the lower Dispensing Tip (4t) of said Liquid Sample Delivery Means (4s) with respect to the Apex (5) of the Elongated Surface Area Providing Essentially Convex Protrusion (2) present within space concentrically defined by said Elongated Dimension Outer Envelope (1). Also shown is a flexible elastic Sample Delivery Hose (19) which is typically utilized to provide Liquid Sample (SS) to a Liquid Sample Inlet Means (4), or to Liquid Sample Delivery Means (4s), (4p) or (4q), where utilized, and a Securing Means (15) for use in securing a user selected position of said Liquid Sample Delivery Means (4s), (4p) or (4q) in said Liquid Sample Inlet Guide Means (4) (4d) and thereby effecting a user-selected gap between said dispensing tip (4t) or (4a) and said apex (5) of said Surface Area Providing Essentially Convex protrusion (2). Said Securing Means (15) is typically composed of an elastic material, (eg. a short section of silicone rubber tubing). Said Securing Means (15) serves to help prevent Carrier Gas (CG) from exiting via Liquid Sample Inlet Means (4), (4d) and (4s) in use.

FIG. 6c shows the upper aspect of a present invention Fractional-Volatization Separator System (GLS) as shown in FIG. 5a2, with an Alternative Liquid Sample Delivery Means (4p), (see also, FIG. 5b2), slid into the upper aspect of the Elongated Dimension Outer Envelope (1) Situated Liquid Sample Inlet Guide Means (4) (4d). It is to be noted that the lower dispensing tip (4a), is the lower aspect of Inner Sample Delivery Tube (4c) which Inner Sample Delivery Tube (4c) has a Protective Jacket (4b) concentrically present therearonund, except at the lower-most extent thereof, (whereat a short section of Inner Sample Delivery Tube (4c) is shown to, extend below and beyond said Outer Protective Jacket (4b), and is identified by (4a). It is noted that the Inner Sample Delivery Tube (4c) and Protective Jacket (4b) can be a single element, but a preferred embodiment is to make the Inner Sample Delivery Tube (4c) of a material such as thin-walled Quartz Capillary tubing, and the Protective Jacket (4b) from a material such as heat-shrinkable Teflon thermally friction bonded to said Sample Delivery Tube (4c). The Inner Sample Delivery Tube (4c) and bonded Outer Protective Jacket (4b) can be secured in a Liquid Sample Inlet Guide Means (4) (4d) by simply being slid thereinto, to form a friction-tight contact with (4d) therein. As well, in the preferred embodiment, FIG. 6c, shows that flexible Securing Means (15) can be utilized, in combination with a precision "Slip-Fit" between the Outer Protective Jacket (4b) and said Liquid Sample Inlet Guide Means (4d). Securing Means (15) also helps seal the identified interconnection against Carrier Gas through the Slip-fit tolerance leakage during use. It is also disclosed that it has been found that the embodiment of FIG. 6c, (wherein the outer diameter of insertable sample delivery means (4p) or (4q) is substantially reduced, so as to reduce elastic stretch of Sample Delivery Hose (19) slid thereover), enables a closer match on Sample Delivery Tube Outer Diameter (O.D.) to Sample Delivery Hose (19) I.D. thereby allowing achieving a more consistent, Liquid Sample entry via flexible elastic Sample Delivery Hose (19). This is because of the presence of a thinner effective (4q) Sample Delivery Tube (4c) wall thickness at (4e), (eg. three (3) mils), and/or the Outer Protective Jacket (4b) taper at (4p) upper extent location (17). Where an effectively thicker walled Liquid Sample Delivery Means, such as Liquid Sample Inlet Means (4) in FIG. 6a, or a Sample Delivery Tube such as (4s) in FIG. 6b is used without a Taper or Graded Outer Diameter Step-Down, (eg. Outer Diameter stepdown from Liquid Sample Inlet (4) to Liquid Sample Delivery Means (4s), (4p) or (4q), preferably including a taper at area (17) of FIG. 6b, (or an upper extent cutaway ares (4e) of FIG. 5b3), it has been found that, particularly during "sample-change", gas bubbles from gas segments introduced into a liquid sample flow stream can become trapped at the area (20) located "ridge", present at the upper extent of said Liquid Sample Delivery Means (4s), (or even more so at ridge area (20) and Liquid Sample Inlet Means (4) or FIG. 6a), and said gas bubbles can unpredictably dislodge and enter the flow of liquid sample which carries a Component/Analyte in use, at a later time during a measurement cycle, as opposed to preferrably flowing directly through the system during a portion of a sample change cycle in which no measurement is being made. (Again, see FIGS. 6a and 6b for visual insight to the presence of an gas bubble trapping horizontal "ridge" in area (20) at the upper aspect of Liquid Sample Inlet Means (4) or Liquid Sample Delivery Means (4s), where flexible elastic Sample Delivery Hose (19) is, without more, simply slidably attached thereto. Also note the substantial reduction is size of the ridge in area (20), by comparing FIGS. 6a and 6b, as well as the essential elimination of said "ridge" in area (17) of FIG. 6c so that it is no more than that of the cross section of the end of Inner Liquid Sample Delivery Tube (4c)) It is emphasized that identified occasional minor "random" detector signal fluctuations, (due to untimely bubble dislodgement from the ridge in area (20)), provided by a detector system into which a Component/Analyte carrying Carrier Gas exiting said Means For Allowing Said Entered Carrier Gas To Exit (8), has been entered, have been essentially eliminated where an Inner Sample Delivery Tube which is thin-walled (as is Liquid Sample Delivery Tube (4c)), or is provided with outer diameter step-down and/or Tapered at location (17) as shown in FIG. 6c, is utilized, and that the present invention embodiment shown in FIGS. 6b, 6c, and 6e demonstrates means by which said problem has been essentially eliminated. Continuing, depending on desired Sample Delivery Hose (19) inside diameter a simple effective alternative to, the shown upper extent taper of the sample delivery means of FIG. 5b2, (used in FIGS. 6c and 6e), is to replace said shown upper extent "Taper" of Protective Jacket (4b) with a simple "Blunt" cutaway of the outer body at upper extent, (as shown in FIG. 5b3), yielding a short section (4e) of exposed thin wall capillary tubing at FIG. 5b3 uppermost extent, (essentially symmetrical with the lower extent section (4a)). Said approach also, eliminates the ridge in area (20) if said Sample Delivery Hose (19) is sufficiently elastic and of appropriate inner diameter, and said approach to eliminating the identified bubble dislodgement problem is within the scope of the invention. It is also noted that where a FIG. 6c embodiment is utilized, the lower extent of the Guide Means (4d) and the lower end of said Protective Jacket (4b) can be oriented so that when mutually vertically aligned, (as shown in FIG. 6c), an initial starting-point "Gap" is defined between the lower aspect of the Dispensing Tip (4a) and the Apex (5) of the Elongated Surface Area Providing Essentially Convex Protrusion (2). This alignment provides good direct visual guidance as to setting the identified "Gap" in use. (See FIG. 6e as well).

It is to be understood that where a Slidably Adjustable Position Liquid Sample Delivery Means (4s) (4p) (4q) is utilized said Guide Means (4) (4d) should be sufficiently elongated to provide favorable aspect registration location, entering accuracy and insertion direction guidance of a Slidably Adjustable Position Liquid Sample Delivery Means (4s) (4p) (4q).

Continuing, FIG. 6d shows the lower aspect of a present invention Fractional-Volatization Separator System (GLS), and in particular shows an Insert (4i) comprising a relatively smaller internal diameter tube than is provided by the Means For Quickly Removing Liquid Sample (6), per se. Also shown is Securing Means in the form of a Flexible Hose similar the flexible Sample Delivery Hose (19) in FIGS. 6a & 6b, which Flexible Hose serves as the "Drain Hose" for rapid removal of residual "spent", "purified", "concentrated" or the like liquid from which has been evaporated volatile or semi-volatile analyte or component. While an Insert (4i) presence is not a requirement of operation, (ie. a Liquid Sample Solution carrying "drain hose" can simply be slid onto the end of the Means For Quickly Removing Liquid Sample (6)), it has been found that when such an internal diameter Restricting Insert is used, a somewhat better pulse-free control over the removal of Liquid Sample Solution arriving at Collection Site (11) can be achieved, particularly where peristaltic pumping, (see FIG. 7), is utilized to effect said removal. That is, said Restricting Insert (4i) serves to dampen pulsations hydraulically induced by an external pump which applies suction to the Means For Quickly Removing Liquid Sample (6).

FIG. 6e shows an expanded scale view of the upper aspect of a present invention Fractional-Volatization Separator System (GLS), shown in combination with a FIG. 5b2 Liquid Sample Delivery Means (4p) comprised of an Inner Sample Delivery Tube (4c) present within a Concentrically Surrounding Jacket (4b) Said Liquid Sample Delivery Means (4p) is shown present within a FIG. 5a2 Liquid Sample Inlet Guide Means, identified as (4) (4d). Note, as described infra, that said Liquid Sample Inlet Guide Means identified as (4) (4d) is of a larger diameter at its upper aspect (4) than at its lower aspect (4d). (Equally acceptable (depending on i.d. and elasticity of Sample Delivery Hose (19)), is a substitution of a FIG. 5b3 Liquid Sample Delivery Means (4q)). This is identified by the space indicated by the identifier (21), but is not a requirement of the present invention. For instance the diameter of the Liquid Sample Inlet guide Means identified by (4) and the lower aspect thereof identified as (4d) an optionally be of one constant diameter, (as in FIGS. 5a15), although this is substantially more difficult to construct utilizing glass blowing technology, where a precision "Slip-Fit" is desired for Liquid Sample Delivery Means (4p). FIG. 6e also shows a Strain Relieving Means (24) present, which Strain Relieving Means (24) is secured via "slide-over" contact to the outer surface of an elastic Securing Means (15) Strain Relieving Means (24) prevents a user from inadvertantly bumping insert (4p) upper extent and cracking inner Sample Delivery Tube (4c) in use. Note also that a Positioning Element (22) is present around, and typically bonded to, the Concentrically Surrounding Outer Jacket (4b) of said Liquid Sample Inlet Means (4p). In use, this Positioning Element (22) is vertically poisitioned on said Liquid Sample Delivery Means (4p) such that when its lower extent rests atop the upper extent of the Liquid Sample Inlet Guide Means identified as (4), the lower extent of the Liquid Sample Delivery Means (4p) Concentrically Surrounding Jacket (4b) is preferably flush, (as identified by numeral (23) with the lower extent of said Liquid Sample Inlet Guide Means identified as (4d), present within said Elongated Dimension Outer Envelope (1). In combination with known fixed (4d) spacing above apex (5) and known fixed (4a) extension below (4b), this arrangement allows an easily achieved desired Gap (G), between the liquid Dispensing Tip (4a) of the Inner Liquid Sample Delivery Tube (4c) and the apex (5) of the Surface Area Providing Essentially Convex Protrusion (2). Note also that the upper aspect f the Liquid Sample Delivery Means (4p) Concentrically Surrounding Jacket (4b) is tapered such that attached flexible Sample Delivery Hose (19) forms elastically thereto in Region (17), thereby minimizing the upper wall end cross section "ridge" at which air bubbles can be trapped during sample change. It is noted that the wall thickness of Inner Liquid Sample Delivery Tube (4c) is typically three (3) mils. (See contrasting discussion and diagram of ridge area (20) with respect to FIGS. 6a and 6b). As noted earlier, depending on desired Sample Delivery Hose (19) inner diameter, a preferred alternative to minimizing said shown uppermost aspect taper if the ridge in area (20) is to replace said uppermost aspect taper of said Sample Delivery Means (4p) (see FIG. 5a2) by a "blunt" ended section cutaway of the Outer Jacket (4b), as in the (4q) embodiment of FIG. 5b3, thereby exposing a section (4e) of thin walled Inner Sample Delivery Tube (4c) at the uppermost extent, in addition to that at the lowermost extent (4a) in FIG. 5b3. Said alternative configuration is shown in FIG. 5a16.

Figure 6N:
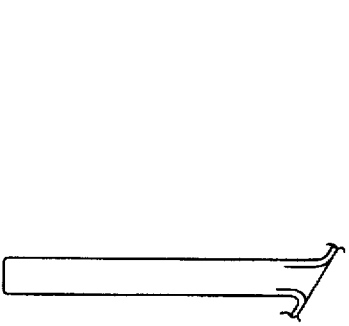
Figure 6O:
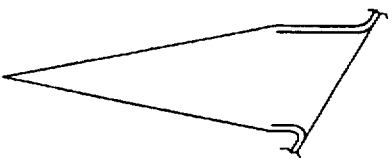
Figure 6P:
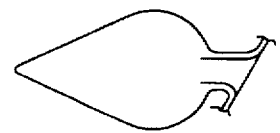
Figure 6Q:
Figure 6V:
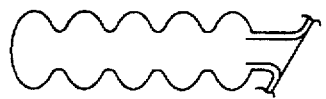
Figure 6A:
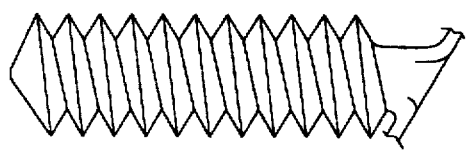
Figure 6U:
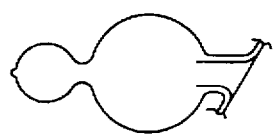
Figure 6Z:
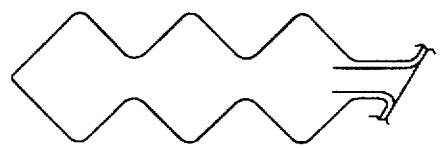
Figure 6T:
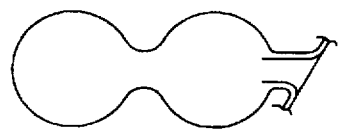
Figure 6Y:
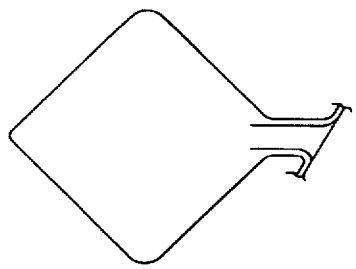
Figure 6S:
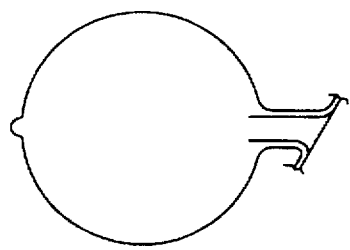
Figure 6X:
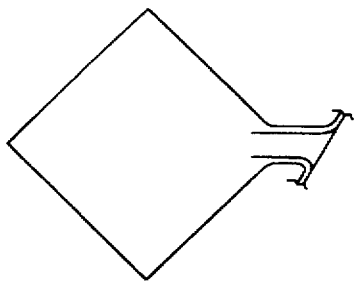
Figure 6R:
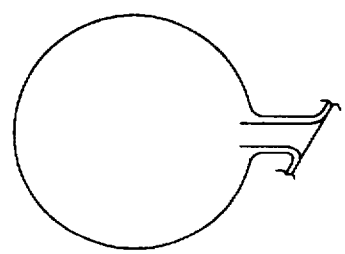
Figure 6W:
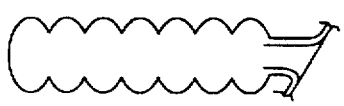

FIGS. 6f through 6m and 6o through 6z show side elevational views, and FIGS. 6n and 6aa perspective views, of various non-limiting exemplary embodiment shapes for the present invention Surface Area Providing Essentially Convex Protrusion (2), as well as the Outer Envelope (1). It is noted that the lower aspect of each embodiment is shown with a sloped base between the left and right sides thereof as viewed, only to be consistent with FIGS. 5a1 and 5a2. Again, while preferred, the lower aspect of the present invention need not provide said slope to be within the scope of the present invention.

It is also noted that it would be possible to operate the present invention Fractional-Volatization Separator System (GLS) with the Carrier Gas entered at the Means For Allowing Carrier Gas To Exit (8), while allowing said entered Carrier Gas to exit at said Means For Entering Carrier Gas (7). Though not preferrable, such a usage is to be considered within the scope of the present invention. In such an embodiment the Means For Entering Carrier Gas will be identified by indentifier (8) or (8') and the Means For Allowing Carrier Gas To Exit by identifier (7) or (7'), with other description provided herein, regarding location etc. unchanged.

Turning now to FIG. 7, there is shown a typical system in which the present invention Fractional-Volatization Separator System (GLS) is utilized for analytical chemistry. Briefly, FIG. 7 shows a non-limiting example of a system designed to detect Mercury Hg in liquid (eg. water, water based, acqueous, acidified acqueous and/or oxidized aqueous), samples. Modified such systems can be utilized to monitor, for instance, organic, organometalic or Volatile Organic Carbon (VOC) analytes in acqeous and/or organic liquids. Continuing, shown are a Robotic Auto-Sampler which can access and change Sample, (which Sample can be chosen from up to three-hundred-sixty (360) different Samples where a CETAC Technologies Auto Sampler System is utilized), and alternatingly access a Rinse or calibration standard, via a Robotic Arm with an affixed liquid (A) "Sipper-Tube" in a controlled, timed, sequence. (Note that the Robotic Arm which moves and the controls the position of the "SipperTube" is identified as (A) and Sipper Tube attached to said Robotic Arm, is identified as (B) where shown accessing Sample 1, and as (C) where accessing unknown Samples (2) through (360), and as (D) where accessing "Rinse" and as (G) where accessing calibration standard solutions (1) through (10)). Also, shown is a reservoir (E) containing Stannous Chloride Reagent. As described in the Background Section of this Disclosure, mixing $Hg^{2+}$ with Stannous Chloride $SnCl_2$ provides a reduced form of Mercury, (ie. $Hg°$), and $Hg°$ is an evaporable form of Mercury thus rendering the sample amenable to processing utilizing the present invention or by any cold vapor style Mercury analysis system. FIG. 7 shows that a Mercury containing Sample and Stannoeus Chloride are entered to a Four Channel Peristaltic Pump System (F) at Y1 and X1, respectively. Exiting said peristaltic pump at (Y2) and (X2) respectively, said liquid sample and stannous chloride streams are joined at a Mixing Tee, which is shown as exterior to said peristaltic pump system. A Liquid Mix which emerges therefrom is caused too enter the present invention Liquid Sample Inlet Means (4) and, as described with respect to, for instance, FIGS. 1–6e, flow over the surface area provided by the Surface Area Providing Essentially Convex Protrusion (2) as a Film (SSF), and be removed from the present invention Fractional-Volatization Separator System (GLS) by way of the Means For Quickly Removing Liquid Sample (6), (which is shown as attached to, a Liquid Drain Tee System and eventually, via Peristaltic Pump (F) Channels Z1 to Z3 and Z2 to Z4 and recombining tee to a Liquid Waste Reservoir). Simultaneous with the flow of Sample Solution (SSF), Carrier Gas (CG) is shown as provided to the (GLS) Means For Entering Carrier Gas (7) by a Carrier Gas supply and Precision Regulator, (not shown), source. Carrier Gas propelled Mercury Vapor evaporated from said (SSF), (comprised in the presently described example of N2 and Hg° Vapor), is shown as exiting the Means For Allowing Said Entered Carrier Gas (8), (which Carrier Gas is accompanied by evaporated Hg° Sample vapor), to exit said present invention Fractional-Volatilization Separator System (GLS) and entering a Mercury Spectrometer and Detector System, which in the present example of mercury is assumed to be a cold vapor mercury absorbance or fluorescence spectrometer, and alternatively an atomic absorption, atomic fluoresence, inductively coupled plasma or inductively coupled plasma-mass spectrometer or the like. It is noted that in use, Carrier Gas (CG) entered to the Means For Entering Carrier Gas (7), exits essentially only through the Means For Allowing Said Entered Carrier Gas to, exit (8) said present invention Fractional-Volatilization Separator System (GLS) This is because Liquid Sample Solution present in said Liquid Sample Solution Inlet Means (4) and Means For Removing Liquid Sample (6) also serves to block. Carrier Gas (CG) flow therethrough in use. In addition, Liquid Sample Solution pumping means attached to said Inlet Means (4) for Introducing Liquid Sample Solution and at said Means For Quickly Removing Liquid Sample (6) also serves to essentially block gas flow therethrough in use. It should be appreciated that Liquid Sample (SS) is typically caused to move through the system of FIG. 7 by a three or four channel Peristaltic Pump (F) System. Typically Liquid Sample (SS) entered to, and exited from the present invention Fractional-Volatilization Separator System (GLS) will be pumped synchronously, (the four pump roller head symbols in FIG. 7 typically actually represent a single head with elongated rollers and four parallel tubes being simultaneously plied by said single set of elongated rollers), with the exiting flow rate being slightly higher than the entry flow rate thereof, (as easily accomplished using one multichannel peristaltic pump with different inner diameter tubes present, in multiple channels, therein). A small, constant amount (less that ten (10%) percent, of carrier gas, it is noted, might be pumped out at said Means For Quickly Removing Liquid Sample (6), along with exiting Liquid Sample, but this is negligible, as it is drawn from the lowest extent of Fractional-Volatilization Separator System (GLS) (wherefrom essentially all of the available sample mercury has already been removed by evaporation from (SSF) at positions higher on said Essentially Convex Protrusion (2) and has been swept upward and away by previously entered carrier gas reaching said higher position earlier in time, prior to said (SSF) reaching said lowest extent Collection Site (11) and Means For Quickly Removing Liquid Sample (6) by pumping therefrom), and in use any such small constant error is compensated for by system calibration under identical fixed conditions with known Mercury content standard solutions prior to analysis of unknown samples. It should also be appreciated that Peristaltic Pump Rollers collapse tubing present in Peristaltic Pumps, hence, provide a seal against Carrier Gas (CG) entered at the Means For Entering Carrier Gas (7) from exiting through the Liquid Sample Inlet Means (4) and the Means for Quickly Removing Liquid Sample (6).

A method of separating volatile/semi-volatile component(s)/analyte(s) present in a liquid component(s)/analyte(s) Containing sample present in a system such as shown in FIG. 7 can include the step of performing analysis of at least one of the constituents of the group consisting of: (the resulting evaporated volatile/semi-volatile component(s)/analyte(s), and the liquid sample from which evaporated volatile/semi-volatile component(s)/analyte(s) have been removed), by use of a detector system selected from the group consisting of: (a fluorescence monitoring detector system, a plasma discharge emission detector system, a plasma mass-spectrometer detector system, a cold vapor mercury atomic absorption detector system, a cold vapor mercury atomic fluorescence detector system, a volatile organic carbon infrared detector system, an organic/organo-metallic molecule infrared spectrophotometry detector system, an organic/organo-metallic molecule mass spectrometer detector system, an organic/organo-metallic molecule inductively coupled plasma detector system, an organic/organo-metallic molecule inductively coupled plasma-mass spectrometer system). In some of the mentioned detector systems, particularly those not employed to, detect mercury, the stannous chloride reagent and its channel (X1-X2) may be omitted along with omitting the mixing "Tee" FIG. 7. For mercury detection common chemical reagents other than $SnCl_2$ may be employed.

In addition, a method f separating volatile/semi-volatile component(s)/analyte(s) present in a liquid component(s) analyte(s) containing sample present in a system such as shown in FIG. 7 can include the step of performing analysis of the resulting volatile/semi-volatile component(s)/analyte (s), said component(s)/analyte(s) being at least one member of the group consisting of a volatile hydride of: (arsenic, bismuth, selenium, antimony and tin), by use of a detector system selected from the group consisting of: (an inductively coupled plasma, an inductively couple plasma-mass spectrometer detector system, an atomic absorption spectrometer, in which case a sodium (or other) borohydride reducing reagent will be substituted for stannous chloride).

It is also noted that said shown Detector System can be of the type that monitors Mercury Vapor Absorbance of a two-hundred-fifty-four (254) nanometer wavelength Electromagnetic Beam from a mercury lamp. In addition said Spectrometer and Detector (DET) system can be an infrared, mass spectrometer, or other monitoring system for volatile organic carbon (VOC) as an evaporated component/analyte from water samples, or other, sample media.

Turning now to FIGS. 8, 9 and 10a, 10b & 10c, there are shown Voltage Recordings from a Chart Recorder attached to a Detector (DET), which was a two-hundred-fifty-four (254 nm) nanometer wavelength Absorbance Monitoring Mercury Spectrometer Detector System, in a system such as shown in FIG. 7. Said results were achieved utilizing a present invention Fractional-Volatilization Separator System (GLS) to detect Mercury levels in Liquid Samples.

FIG. 8, shows Water Sample Calibration Absorbance Values sequentially achieved by the present invention, wherein known Standard Mercury Water Solutions of one-half (0.5), one (1.0), two (2.0) and five (5.0) Parts-per-billion (PPB) mercury content were analyzed with each Standard test being repeated five (5) times in sequence. The Carrier Gas Flow Rate was three-hundred (300) mL/min) and thirty (30) second autosampler uptake and rinse periods were utilized. It is to be appreciated that excellent "Peak Shape" waveforms are present, as determined by sharp rise and fall times, low noise, exceptional signal stability and peak plateau reproducibility of the Mercury concentration determination. FIG. 8 shows that a signal rise and stabilization occurs within a few seconds, (typically 6-20 seconds), and after each sampling period is over, the sample washout (preceding the next sample), also proceeds within a few seconds. It is to be noted that FIG. 8 demonstrates operation of the present invention Fractional-Volatilization Separator System (GLS) in what is termed a "Normal-Throughput" Mode, characterized by analysis rates of one (1) sample per minute.

FIG. 9 shows operation of a present invention Fractional-Volatilization Separator System (GLS)in a "High-Sensitivity" Mode. This Mode if operation is effected by lowering the Carrier-Gas Flow Rate to thirty (30) (mL/min) and increasing a utilized Voltage Chart Recorder "Voltage-Gain" (proportional to Absorbance). While longer Sample Uptake and Rinse times are required, (eg. ninety (90) seconds each for this mode), it is to, be noted that exceptional signal sensitivity is achieved for the very low Mercury Concentrations of (0.010 PPB), (0.020 PPB) and (0.050 PPB). It has been determined that a detection limit of slightly below one part per trillion (0.001 PPB), (actually 0.00086 PPB or 0.86 Parts-Per-Trillion, PPT is the detection limit), is achievable by use of the present invention Fractional- Volatilization Separator System (GLS). In contrast, known commercially available Cold Vapor Mercury Absorption Photometer Systems typically yield Detections Limits on the order of ten (10) to twenty (20) times higher, (ie. worse), where Direct Absorbance Readout is utilized, (as with the present invention) and, for instance, non-EPA approved gold amalgam preconcentration is not performed.

Figure 10C:
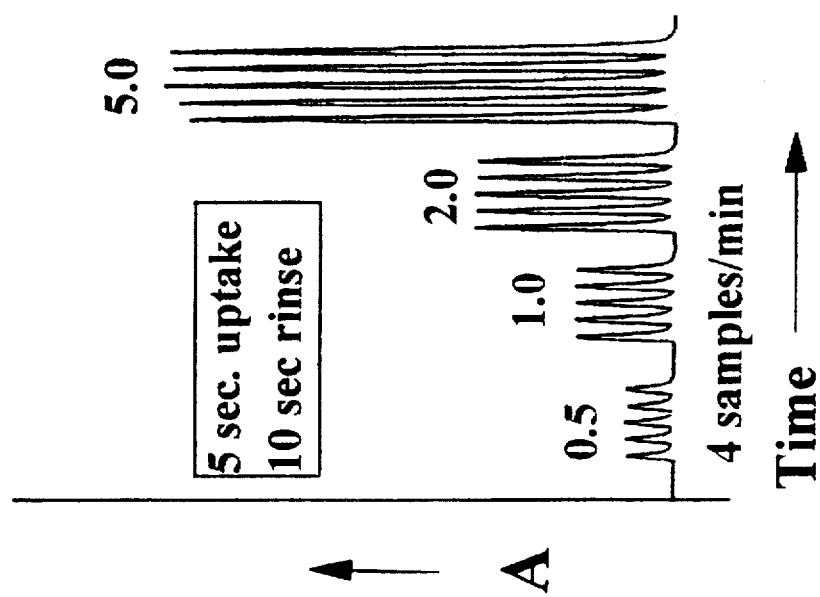

FIGS. 10a, 10b and 10c show operation of the present invention Fractional-Volatilization Separator System (GLS) in several "Accelerated Throughput" Modes yielding Absorbance Detector System provided Absorbance results provided by application of a present invention Fractional-Volatilization Separator System (GLS) system in a System as demonstrated by FIG. 7. Note that three Data Groups are presented. Data obtained utilizing two (2), Three (3) and Four (4) Samples-Per-Minute are presented. These varied Accelerated Sample Throughput Rates are achieved by adjustment of Carrier Gas Flow Rate and Autosampler Uptake and Rinse Times. Sample Uptake and Rinse Times for each Data Group are provided in FIGS. 10a, 10b and 10c and are, for FIG. 10a, ten (10) and twenty (20) seconds respectively; for FIG. 10b, eight (8) and twelve (12) seconds respectively; and for FIG. 10c, five (5) and ten (10) seconds respectively. In all of the FIG. 10a, 10b and 10c cases, the Carrier Gas Flow Rate was three-Hundred (300 ) Milliliters-per-minute, (mL/min). The System of FIG. 7, it is noted provides Liquid Sample Solution to a present invention Fractional-Volatilization System (GLS) via an Auto-Sampler Robotic Arm (A) and attached "Sipper-Tube" which is immersed in an Unknown Sample, known Calibration Standard, or Blank Rinse for the indicated time periods. The very important result to note is that only in FIG. 10c, and at concentration levels of five (5.0) part-per-billion (PPB), is any indication of non-repeatability detected, (eg. note the FIG. 10c variation in Absorbance Peak Magnitudes at five (5.0) PPB). Thus, at a Carrier Gas Flow Rate of 300 (mL/m), repeatable detection of Mercury at all levels below five (5.0) (PPB) is demonstrated, at the unprecedented throughput rate of Up to four (4) samples per minute. It is noted, but not shown in any FIGURE, that where even higher Carrier Gas Flow Rates, (eg. 500 mL/min), are utilized, even better results are obtained with good reproducibility at all tested concentrations including five (5.0) PPB, for even the case of four (4) sample/minute throughput. It is instructive, in comparison, to note that the best results known to be achievable by presently marketed competitor produced systems provide satisfactory wash-out and repeatability in results, at approximately maximum rates of only One-Half (½) to One (1.0) Sample-Per-Minute, emphasis added. The present invention is thus shown to be four (4) times faster in providing cold vapor mercury determination than the best prior art systems.

(It is noted that the vertical axis units of Absorbance (A) in the above described FIGS. 8, 9 and 10a through 10c examples are arbitrary, and that said Absorbance represents results achieved utilizing Two-Hundred-Fifty-Four (254) nanometer wavelength electromagnetic radiation). The horizontal axis in each of said FIGS. 8, 9 and 10a, 10b and 10c, it is noted, represents time.

Continuing, it is of importance to note that said Surface Area provided by said Elongated Surface Area Providing Essentially Convex Protrusion (2) is sheltered from the environment by the space encompassed within said Elongated Dimension Outer Envelope (1). This, in combination with the ability of the present invention Fractional-Volatilization Separator System to provide an even, continuous, essentially constant surface area/volume ratio, Film of Liquid or Liquid Component/Analyte Containing sample solution (SSF) over said Surface Area, is an important attribute of the present invention Fractional-Volatilization separator as it allows stabilization of, and optional precise control over the temperature of said Film (SSF) of Liquid Component/Analyte Containing Sample Solution in use, and therefore over what Component(s)/Analyte(s) are evaporated therefrom during a Luser determined period, and stabilization of, and optional precise control over the rate of Component/Analyte evaporation, as is required.

It is also to be understood that the terminology "Film" is to be interpreted to include Thin and Thick "Films", or even what might be considered a "Flood" of Liquid Sample (SS) as it flows over the Surface Area Providing Conves Protrusion (2).

It should also be appreciated that the present invention Fractional-Volatilization Separator System (GLS) can be dimensioned to handle analytical chemistry needs, as well as to allow use in industrial settings where a liquid component containing Sample Solution is to be evaporated or "purified" of unwanted volatile components or alternatively caused to contain a higher concentration of desired non-volatile components. In particular, in the foregoing, the term "Analyte" Was used to, refer to an analytical chemistry usage and the term "Component" was used to refer to an industrial usage of the present invention Fractional-Volatilization Separator system (GLS). The terms "Analyte" and "Component" are to be considered as functionally essentially equivalent for the purposes of Claim interpretation.

It is also, to be understood that while the term "Sample Solution" has been utilized to describe Component/Analyte presence in a liquid, said term "Sample Solution" is to be interpreted sufficiently broad so as to: include Liquid Mixtures, Gas-Liquid Dispersions, Emulsions and the like, in addition to true Component/Analyte containing solutions for the purposes of Claim construction. As well, the terminology such as "Sample Solution from which said Component/Analyte has been removed" and "Liquid Sample Solution from which has been evaporated volatile Component/Analyte" is to be interpreted to include "Residual", "Spent", "Concentrated", "Enriched", "Purified" etc., as is appropriate to describe the liquid removed for various purposes at said Means for Quickly Removing Liquid Sample (6) in a specific application.

It is noted as well, that the terminology "Continuous" as applied to the flow of a Liquid Sample Solution flow over the Surface Area provided by a Essentially Convex Protrusion (2), is to be understood to mean that said Flow is "Continuous" over a designated application period and synchronized period of data acquisition. That is, the Flow of a Liquid Sample or Rinse etc. is "Continuous" while applied, which can be on a periodic basis, in which many periods of "Continuous" Flow are effected, for instance, from different samples introduced sequentially for brief periods, each ranging from approximately five (5) to one-hundred-twenty (120) seconds or more, or from different standard calibration solutions, or from blank solutions as the case may be.

It is further noted that the terminology "Volatile Component/Analyte" is too be interpreted to include "Semi-volatile Component/Analyte", the distinction being focused upon the relative ease, or at what temperature, with which a Component/Analyte can be removed from a Liquid Sample Solution, and over which temperature control can be exercised.

It is also, noted that the terminology "Fractional-Volatilization Separator System" is to be interpreted sufficiently broadly so as to include a Gas-Liquid Separator system in which a simple Gas-Liquid separation process, (eg. mercury, arsine, stannous, hydrogen, selenide, etc. evaporation from reduced), Occurs, as well as to systems which serve to separate volatile, (eg. volatile organic carbon), or semi-volatile, liquid organic or organo-metallic Component(s)/Analyte(s) from a liquid.

It is also to be understood that the descriptive terminology upward protruding "surface area providing essentially convex protrusion" is to be interpreted to comprise essentially rod, essentially sharpened pencil, essentially blunt pencil, essentially closed top cylinder, essentially spherical, essentially hemispherical, essentially pyramidal, essentially Washington Monument shape, essentially closed top hour-glass, essentially closed top multiple repeating hour-glass, essentially conical, essentially bullet, essentially helical screw-thread and other functional shapes, including any combinations of thereof, with essentially rounded, essentially conical, essentially nippled or other functional shape, in addition to, or instead of being elongated. The only requirement being that the overall shape is generally essentially convex and upwardly protruding, with a closed apex.

It is also to be understood that the Fractional-Volatilization separator system (GLS) of the present invention can be easily fabricated by well known glass-blowing techniques, or it can be fabricated from metal, ceramic, or, for instance, organo-polymers, including fluoropolymers.

It is additionally noted that the terminology describing the interconnection between an Outer Envelope (1), and a Surface Area Providing Essentially Convex Protrusion (2) as "essentially continuous", should be interpreted to include a result effected by a "joining of" separate elements, perhaps by gluing or thermal bonding, or by use of interconnecting means, (eg. "O" Rings), as well as a result effected by forming an Outer Envelope (1), and a Surface Area Providing Essentially Convex Protrusion (2) as from a single continuous piece of material.

From the foregoing, it should be appreciated that the preferred embodiment of the present invention Fractional-Volatilization Separator System can be, but does not need be, of simple, rigid, one, two, or multiple piece construction which is easy to manufacture, provides wetting sample component or analyte evaporation Surface Areas, allows optional highly efficient and accurate internal temperature control, allows continuous operation, and provides smooth stable component or analyte vapors over time, and is quick and easy to wash-out in preparation for subsequent usage with different samples. For instance, a two or three-piece molded construction can be produced.

In addition, it should be appreciated that enhanced detection of trace amounts of sample component or analyte are made possible, and stable, repeatable precision and accuracy of analytical instruments with which said present invention Fractional-Volatilization Separator System is used, can be improved thereby without interference by foaming effects of any kind, regardless of the liquid medium properties (even a solution of fish tissue digest, or laundry detergent solution does not foam in the present invention Fractional-Volatilization Separator System). As well, with larger scale dimensions, the system of the present invention can be utilized in industrial scale phase separation liquid purification procedures, (including sub-boiling distillation and the desalination of water), as well as in the preparation of liquid concentrates.

Finally, for convenience, the Claims utilize the following basic terminology to identify elements of the present invention fractional-volatilization separator (GLS) as demonstrated in the FIGURES:

element (1)—"outer envelope";

element (2)—"inner protrusion";

element (3)—"sample delivery means"

element (4)—"liquid sample inlet means";

element (5)—"the apex of the inner protrusion";

element (6)—"means for removing liquid sample from the liquid collection site";

element (7)—"means for introducing a flow of carrier gas into the enclosed space";

element (8)—"means for removing carrier gas and evaporated volatile-semivolatile component(s)/analyte(s) from the enclosed space";

element (9)—"hollow inner protrusion space"

element (10)—"where said outer envelope and said inner protrusion are joined";

element (11)—"liquid collection site".

Also, the terminology "volatile component(s)" is to be read sufficiently broad to include "volatile and semivolatile"analyte(s) and semivolatile component(s).

Having hereby disclosed the subject matter of the present invention, it should be apparent that many modifications, substitutions, and variations of the present invention are possible in light thereof. It is therefore to be understood that the invention may be practiced other than as specifically described, and should be limited in breadth only by the Claims.

I claim:

1. A fractional-volatilization separator system comprising:

an enclosed space formed from an outer envelope and an inner protrusion centrally located within said outer envelope, lower ends of said outer envelope and said inner protrusion being joined together to form a liquid collection site; said outer envelope having a substantially closed upper end and said inner protrusion having a closed upper end with an apex thereat;

liquid sample inlet means in the outer envelope for introducing a liquid sample, which contains volatile components, at the apex of the inner protrusion, said inner protrusion and apex having a shape which causes liquid sample to uniformly spread and flow downward over the inner protrusion as a volatile components evaporation enhancing film;

means for removing liquid sample from said collection site, located adjacent to said collection site in said outer envelope or where said outer envelope and said inner protrusion are joined;

means for introducing a flow of carrier gas into said enclosed space, located in said outer envelope or said inner protrusion; and means for removing the carrier gas and the evaporated volatile components from the enclosed space, located in the outer envelope;

said means for removing the carrier gas and evaporated volatile components from the enclosed space being located vertically above the location of the means for introducing a flow carrier gas into said enclosed space, and said means for introducing a flow of gas into said enclosed space being located vertically above said means for removing liquid sample from said collection site.

2. The fractional-volatilization separator system as in claim 1, in which the outer envelope and the inner protrusion are each of a substantially elongated cylindrical shape, with said apex being rounded.

3. The fractional-volatilization separator system as in claim 1 in which the inner protrusion has a surface treated to make the surface phillic with respect to the sample by a method selected from the group consisting of physical surface roughening, sand blasting, frosting, acid etching, silanization, and chemical treatment.

4. The fractional-volatilization separator system as in claim 1, in which the inner protrusion is hollow and is optionally filled with one or more elements selected from the group consisting of insulating material, gas, fluid, paste and gel.

5. The fractional-volatilization separator system as in claim 1, in which the inner protrusion is hollow and optionally contains temperature control means selected from the group consisting of heating means, cooling means and temperature stabilizing means.

6. The fractional-volatilization separator system as in claim 1, in which said liquid sample inlet means is located in said outer envelope at or adjacent to the substantially closed upper end thereof.

7. The fractional-volatilization separator system as in claim 1, in which said means for introducing a flow of carrier gas is in said outer envelope.

8. The fractional-volatilization separator system as in claim 1, in which said means for introducing a flow of carrier gas is in said inner protrusion.

9. The fractional-volatilization separator system as in claim 1, in which at least one of said means for introducing a flow of carrier gas or said means for removing carrier gas is constructed to direct the carrier gas around or along said inner protrusion in an upward direction.

10. The fractional-volatilization separator system as in claim 1, in which said outer envelope and said inner protrusion are constructed as a single unitary piece.

11. The fractional-volatilization separator system as in claim 1, in which said outer envelope and said inner protrusion are of multi-piece construction.

12. The fractional-volatilization separator system as in claim 1, in which said liquid sample inlet means comprises a liquid sample delivery means capable of movement relative to the apex of said inner protrusion for changing a distance between the liquid sample delivery means and the apex of said inner protrusion.

13. The fractional-volatilization separator system as in claim 12, in which said liquid sample inlet means further comprises a guide means for slidably retaining said liquid sample delivery means.

14. The fractional-volatilization separator system as in claim 13, in which said liquid sample delivery means comprises an inner sample delivery tube encompassed by an outer protective jacket.

15. The fractional-volatilization separator system as in claim 14, in which said inner sample delivery tube has a wall thickness less than a wall thickness of said guide means.

16. The fractional-volatilization separator system as in claim 14, in which said outer protective jacket comprises a heat shrinkable material.

17. The fractional-volatilization separator system as in claim 16, in which said heat shrinkable material is a polytetrafluoroethylene material.

18. The fractional-volatilization separator system as in claim 13, in which said liquid sample delivery means further comprises a positioning element for coacting with said guide means to set the distance between the liquid sample delivery means and the apex of said inner protrusion.

19. The fractional-volatilization separator system as in claim 1, which further comprises and inner diameter restricting insert present in said means for removing liquid sample from said liquid collection site.

20. The fractional-volatilization separator system as in claim 1, in which said means for introducing a flow of carrier gas into the enclosed space is located adjacent to the lower end of said outer envelope or said inner protrusion.

21. A method of separating volatile components present in a liquid sample comprising, the steps of:

a) providing a fractional-volatilization separator system comprising:

an enclosed space formed from an outer envelope and an inner protrusion centrally located within said outer envelope, lower ends of said outer envelope and said inner protrusion being joined together to form a liquid collection site; said outer envelope having a substantially closed upper end and said inner protrusion having a closed upper end with an apex thereat;

liquid sample inlet means in the outer envelope for introducing a liquid sample, which contains volatile components, at the apex of the inner protrusion, said inner protrusion and apex having a shape which causes liquid sample to uniformly spread and flow downward over the inner protrusion as a volatile components evaporation enhancing film;

means for removing liquid sample from said collection site, located adjacent to said collection site in said outer envelope or where said outer envelope and said inner protrusion are joined;

means for introducing a flow of carrier gas into said enclosed space, located in said outer envelope or said inner protrusion; and means for removing the carrier gas and the evaporated volatile components from the enclosed space, located in the outer envelope;

said means for removing the carrier gas and evaporated volatile components from the enclosed space being located vertically above the location of the means for introducing a flow carrier gas into said enclosed space, and said means for introducing a flow of gas into said enclosed space being located vertically above said means for removing liquid sample from said collection site;

b) continuously introducing said liquid sample to the apex of the inner protrusion;

c) continuously introducing a carrier gas into the enclosed space through said means for introducing a flow of carrier gas;

d) continuously removing separated volatile components and carrier gas from the enclosed space through said means for removing the carrier gas and the evaporated volatile components from the enclosed space; and e) continuously causing liquid sample from which volatile components have been removed to be removed upon reaching the liquid collection site by said means for removing liquid sample.

22. The method of separating volatile components present in a liquid sample as in claim 21 in which at the carrier gas is introduced into the enclosed space in a manner that it will flow around or along said inner protrusion in an upward direction.

23. The method of separating volatile components present in a liquid sample as in claim 21, in which water is the volatile component and the liquid sample is salt water.

24. The method of separating volatile components present in a liquid sample as in claim 21, in which mercury is the volatile component.

25. The method of separating volatile components present in a liquid sample as in claim 21, in which volatile organic compounds are the volatile components.

26. The method of separating volatile components present in a liquid sample as in claim 21, further comprising analyzing one of the volatile components or the liquid sample removed from the collection site.

27. The method of separating volatile components present in a liquid sample as in claim 26, in which the volatile components are analyzed by a detector selected from the group consisting of a plasma emission detector and a plasma-mass spectrometer, said volatile components containing at least one hydride selected from the group consisting of hydrides of arsenic, bismuth, selenium, antimony, and tin.

28. The method of separating volatile components present in a liquid sample as in claim 26, in which the analyzing step is performed with a detector selected from the group consisting of a fluorescence detector, a plasma discharge emission detector, a mass spectrometer, a cold vapor mercury atomic absorption detector, a cold vapor mercury atomic fluorescence detector, an infrared detector, a plasma-mass spectrometer, and an electromagnetic energy absorption detector.

29. The method of separating volatile components present in a liquid sample as in claim 21, in which a peristaltic pump is used in at least one of continuously introducing said liquid sample to the apex of the inner protrusion or continuously causing liquid sample from which volatile components have been removed to be removed from the liquid collection site.

30. The method of separating volatile components present in a liquid sample as in claim 21, in which a rate of continuously introducing said liquid sample to the apex of the inner protrusion is slower than a rate of continuously causing liquid sample from which volatile components have been removed to be removed from the liquid collection site.

* * * * *